(12) United States Patent
Onoue et al.

(10) Patent No.: US 7,332,473 B2
(45) Date of Patent: Feb. 19, 2008

(54) PEPTIDES AND MEDICINAL COMPOSITIONS CONTAINING THE SAME

(75) Inventors: Satomi Onoue, Ibaraki (JP); Kousuke Endo, Ibaraki (JP); Asami Matsumoto, Ibaraki (JP)

(73) Assignee: Itoham Foods Inc., Kobe-shi (JP)

( * ) Notice: Subject to any disclaimer, the term of this patent is extended or adjusted under 35 U.S.C. 154(b) by 0 days.

(21) Appl. No.: 10/536,880

(22) PCT Filed: Nov. 21, 2003

(86) PCT No.: PCT/JP03/14924

§ 371 (c)(1),
(2), (4) Date: May 27, 2005

(87) PCT Pub. No.: WO2004/048401

PCT Pub. Date: Jun. 10, 2004

(65) Prior Publication Data

US 2006/0276384 A1    Dec. 7, 2006

(30) Foreign Application Priority Data

Nov. 27, 2002  (JP) .............................. 2002-344523

(51) Int. Cl.
  *A61K 38/00*   (2006.01)
  *C07K 5/00*    (2006.01)
  *C07K 7/00*    (2006.01)

(52) U.S. Cl. ................ 514/12; 514/2; 424/185.1; 530/300; 530/324

(58) Field of Classification Search ................ None
See application file for complete search history.

(56) References Cited

U.S. PATENT DOCUMENTS

| 4,939,224 | A   |   | 7/1990 | Musso et al. |
| 5,141,924 | A   | * | 8/1992 | Bolin ............................ 514/12 |
| 6,242,563 | B1  | * | 6/2001 | Dong ........................... 530/300 |

FOREIGN PATENT DOCUMENTS

| EP | 0 241 926  | 10/1987 |
| EP | 0 529 487  | 3/1993  |
| EP | 0 613 904  | 9/1994  |
| EP | 0 796 867  | 9/1997  |
| EP | 1 462 112  | 9/2004  |
| JP | 11-100399  | 4/1999  |
| JP | 2001-226284| 8/2001  |
| JP | 2003-73301 | 3/2003  |
| WO | 89/05857   | 6/1989  |
| WO | 03/051387  | 6/2003  |

OTHER PUBLICATIONS

Masayoshi Onoe et al., "VIP/PACAP Yudotai no Kozo Kassei Sokan—N Tanbu no Rittai Kozo Kenkyu-", The Pharmaceutical Society of Japan, Dai 119 Nenkai Yoshishu 1999, vol. 119, No. 3, p. 69, (30[PV] 10-016).

K. Kashimoto et al., "Structure-Activity Relationship Studies of PACAP-27 and VIP Analogues" Peptide Chemistry, 33rd, pp. 361-364, 1995.

K. Kashimoto et al., "Structure-Activity Relationship Studies of PACAP-27 and VIP Analogues" Annals New York Academy of Sciences, vol. 805, pp. 505 to 510, (VIP, PACAP and Relatated Peptides), 1996.

A. Okazawa et al., "Effect of a novel PACAP-27 analogue on muscarinic airway responsiveness in guinea-pigs in vivo" European Respiratory Journal, vol. 12, No. 5, pp. 1062 to 1066, 1998.

M. O'Donnell et al., Structure-Activity Studies of Vasoactive Intestinal Polypeptide, The Journal of Biological Chemistry, vol. 266, No. 10, pp. 6389 to 6392, 1991.

Gozes et al., "Mapping the Active Site in Vasoactive Intestinal Peptide to a Core of Four Amino Acids: Neuroprotective Drug Degisn", Proceedings of the National Acedemy of Sciences of USA, vol. 96, No. 7 pp. 4143-4148 (1999).

Carlquist, et al., "Isolation and Amino Acid Composition of Human Vasoactive Intestinal Polypeptide VIP", Horm. Metabol. Res. 14, pp. 28-29. 1982.

\* cited by examiner

*Primary Examiner*—Anish Gupta
*Assistant Examiner*—Julia Ha
(74) *Attorney, Agent, or Firm*—Oblon, Spivak, McClelland, Maier & Neustadt, P.C.

(57) ABSTRACT

This invention provides a pharmaceutical composition comprising, as an active ingredient, a peptide derived from a PACAP or VIP peptide or a pharmaceutically acceptable salt thereof. This invention provides a PACAP/VIP derivative that can inhibit tautomerization in a solution and that can be applied to clinical applications over a long period of time. Such peptides are useful for ameliorating symptoms of diseases, such as regressive neurodegenerative diseases, erectile dysfunction, and bronchial asthma.

18 Claims, 6 Drawing Sheets

(A)

Addition of sample

Addition of carbachol (B)

Addition of sample

Addition of carbachol (C)

Addition of sample

Addition of carbachol

SEQUENCE LISTING

```
<160> NUMBER OF SEQ ID NOS: 34

<210> SEQ ID NO 1
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (5)..(5)
<223> OTHER INFORMATION: Xaa = Val or Ile
<220> FEATURE:
<221> NAME/KEY: MISC_FEATURE
<222> LOCATION: (8)..(8)
<223> OTHER INFORMATION: Xaa = Asp, Glu or Ala
<220> FEATURE:
<221> NAME/KEY: MISC_FEATURE
<222> LOCATION: (9)..(9)
<223> OTHER INFORMATION: Xaa = Asn or Ser
<220> FEATURE:
<221> NAME/KEY: MISC_FEATURE
<222> LOCATION: (11)..(11)
<223> OTHER INFORMATION: Xaa = Thr or Ser
<220> FEATURE:
<221> NAME/KEY: MISC_FEATURE
<222> LOCATION: (13)..(13)
<223> OTHER INFORMATION: Xaa = Leu or Tyr
<220> FEATURE:
<221> NAME/KEY: MISC_FEATURE
<222> LOCATION: (15)..(15)
<223> OTHER INFORMATION: Xaa = Lys or Arg
<220> FEATURE:
<221> NAME/KEY: MISC_FEATURE
<222> LOCATION: (17)..(17)
<223> OTHER INFORMATION: Xaa = Leu or Nle
<220> FEATURE:
<221> NAME/KEY: MISC_FEATURE
<222> LOCATION: (20)..(20)
<223> OTHER INFORMATION: Xaa = Lys or Arg
<220> FEATURE:
<221> NAME/KEY: MISC_FEATURE
<222> LOCATION: (21)..(21)
<223> OTHER INFORMATION: Xaa = Lys or Arg
<220> FEATURE:
<221> NAME/KEY: MISC_FEATURE
<222> LOCATION: (26)..(26)
<223> OTHER INFORMATION: Xaa = Ile or Val
<220> FEATURE:
<221> NAME/KEY: misc_feature
<222> LOCATION: (27)..(27)
<223> OTHER INFORMATION: Xaa can be any naturally occurring amino acid

<400> SEQUENCE: 1

His Ser Asp Ala Xaa Phe Thr Xaa Xaa Tyr Xaa Arg Xaa Arg Xaa Gln
1               5                   10                  15

Xaa Ala Val Xaa Xaa Tyr Leu Ala Ala Xaa Xaa
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (28)..(28)
<223> OTHER INFORMATION: Amidation

<400> SEQUENCE: 2

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 3
<211> LENGTH: 27
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MOD_RES
<222> LOCATION: (27)..(27)
<223> OTHER INFORMATION: Amidation

<400> SEQUENCE: 3

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 4
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (38)..(38)
<223> OTHER INFORMATION: Amidation

<400> SEQUENCE: 4

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
            35

<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (31)..(31)
<223> OTHER INFORMATION: Amidation

<400> SEQUENCE: 5

His Ser Asp Ala Val Phe Thr Asp Asn Tyr Thr Arg Leu Arg Arg Gln
1               5                   10                  15

Leu Ala Val Arg Arg Tyr Leu Asn Ser Ile Leu Asn Gly Arg Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (30)..(30)
<223> OTHER INFORMATION: Amidation

<400> SEQUENCE: 6

His Ser Asp Gly Ile Phe Thr Asp Ser Tyr Ser Arg Tyr Arg Arg Gln
1               5                   10                  15

Leu Ala Val Arg Arg Tyr Leu Ala Ala Val Leu Gly Arg Arg
            20                  25                  30

<210> SEQ ID NO 7
<211> LENGTH: 38
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (38)..(38)
<223> OTHER INFORMATION: Amidation

<400> SEQUENCE: 7

His Ser Asp Gly Ile Phe Thr Asp Ser Tyr Ser Arg Tyr Arg Arg Gln
1               5                   10                  15

Leu Ala Val Arg Arg Tyr Leu Ala Ala Val Leu Gly Arg Arg Tyr Arg
            20                  25                  30

Gln Arg Val Arg Asn Arg
        35

<210> SEQ ID NO 8
<211> LENGTH: 25
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (25)..(25)
<223> OTHER INFORMATION: Amidation

<400> SEQUENCE: 8

His Ser Asp Ala Val Phe Thr Asp Asn Tyr Thr Arg Leu Arg Lys Gln
1               5                   10                  15

Met Ala Val Lys Lys Tyr Leu Asn Ser
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (17)..(17)
<223> OTHER INFORMATION: Oxidation

<400> SEQUENCE: 9

His Ser Asp Ala Val Phe Thr Asp Asn Tyr Thr Arg Leu Arg Lys Gln
1               5                   10                  15

Met Ala Val Lys Lys Tyr Leu Asn Ser
            20                  25

<210> SEQ ID NO 10
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (23)..(23)
<223> OTHER INFORMATION: Amidation

<400> SEQUENCE: 10

His Ser Asp Ala Val Phe Thr Asp Asn Tyr Thr Arg Leu Arg Lys Gln
1               5                   10                  15

Leu Ala Val Lys Lys Tyr Leu
            20
```

```
<210> SEQ ID NO 11
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (23)..(23)
<223> OTHER INFORMATION: Amidation

<400> SEQUENCE: 11

His Ser Asp Ala Val Phe Thr Asp Asn Tyr Thr Arg Leu Arg Arg Gln
1               5                   10                  15

Leu Ala Val Arg Arg Tyr Leu
            20

<210> SEQ ID NO 12
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (28)..(28)
<223> OTHER INFORMATION: Amidation

<400> SEQUENCE: 12

His Ser Asp Ala Val Phe Thr Asp Asn Tyr Thr Arg Leu Arg Lys Gln
1               5                   10                  15

Leu Ala Val Lys Lys Tyr Leu Ala Ala Ile Leu Asn
            20                  25

<210> SEQ ID NO 13
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (30)..(30)
<223> OTHER INFORMATION: Amidation

<400> SEQUENCE: 13

His Ser Asp Ala Val Phe Thr Asp Asn Tyr Thr Arg Leu Arg Arg Gln
1               5                   10                  15

Leu Ala Val Arg Arg Tyr Leu Ala Ala Ile Leu Gly Arg Arg
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Acylation
<220> FEATURE:
<221> NAME/KEY: MOD_RES
<222> LOCATION: (30)..(30)
<223> OTHER INFORMATION: Amidation

<400> SEQUENCE: 14

His Ser Asp Ala Val Phe Thr Asp Asn Tyr Thr Arg Leu Arg Arg Gln
```

```
                1               5                  10                 15
Leu Ala Val Arg Arg Tyr Leu Ala Ala Ile Leu Gly Arg Arg
            20                  25                 30

<210> SEQ ID NO 15
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: LIPID
<222> LOCATION: (1)..(1)
<223> OTHER INFORMATION: sterate
<220> FEATURE:
<221> NAME/KEY: MOD_RES
<222> LOCATION: (30)..(30)
<223> OTHER INFORMATION: amidation

<400> SEQUENCE: 15

His Ser Asp Ala Val Phe Thr Asp Asn Tyr Thr Arg Leu Arg Arg Gln
1               5                  10                 15

Leu Ala Val Arg Arg Tyr Leu Ala Ala Ile Leu Gly Arg Arg
            20                  25                 30

<210> SEQ ID NO 16
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 16

His Ser Asp Ala Val Phe Thr Asp Asn Tyr Thr Arg Leu Arg Arg Gln
1               5                  10                 15

Leu Ala Val Arg Arg Tyr Leu Ala Ala Ile Leu Gly Arg Arg
            20                  25                 30

<210> SEQ ID NO 17
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (17)..(17)
<223> OTHER INFORMATION: Xaa = Nle
<220> FEATURE:
<221> NAME/KEY: MOD_RES
<222> LOCATION: (30)..(30)
<223> OTHER INFORMATION: Amidation

<400> SEQUENCE: 17

His Ser Asp Ala Val Phe Thr Asp Asn Tyr Thr Arg Leu Arg Arg Gln
1               5                  10                 15

Xaa Ala Val Arg Arg Tyr Leu Ala Ala Ile Leu Gly Arg Arg
            20                  25                 30

<210> SEQ ID NO 18
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (28)..(28)
```

<223> OTHER INFORMATION: Amidation

<400> SEQUENCE: 18

His Ser Asp Ala Val Phe Thr Asp Asn Tyr Thr Arg Leu Arg Arg Gln
1               5                   10                  15

Leu Ala Val Arg Arg Tyr Leu Ala Ala Ile Leu Gly
            20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (29)..(29)
<223> OTHER INFORMATION: Amidation

<400> SEQUENCE: 19

His Ser Asp Ala Val Phe Thr Asp Asn Tyr Thr Arg Leu Arg Arg Gln
1               5                   10                  15

Leu Ala Val Arg Arg Tyr Leu Ala Ala Ile Leu Gly Lys
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (29)..(29)
<223> OTHER INFORMATION: Amidation

<400> SEQUENCE: 20

His Ser Asp Ala Val Phe Thr Asp Asn Tyr Thr Arg Leu Arg Arg Gln
1               5                   10                  15

Leu Ala Val Arg Arg Tyr Leu Ala Ala Ile Leu Gly Arg
            20                  25

<210> SEQ ID NO 21
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (30)..(30)
<223> OTHER INFORMATION: Amidation

<400> SEQUENCE: 21

His Ser Asp Ala Val Phe Thr Asp Asn Tyr Thr Arg Leu Arg Arg Gln
1               5                   10                  15

Leu Ala Val Arg Arg Tyr Leu Ala Ala Ile Leu Gly Lys Arg
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES

```
<222> LOCATION: (30)..(30)
<223> OTHER INFORMATION: Amidation

<400> SEQUENCE: 22

His Ser Asp Ala Val Phe Thr Glu Asn Tyr Thr Arg Leu Arg Arg Gln
1               5                   10                  15

Leu Ala Val Arg Arg Tyr Leu Ala Ala Ile Leu Gly Arg Arg
            20                  25                  30

<210> SEQ ID NO 23
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (23)..(23)
<223> OTHER INFORMATION: Amidation

<400> SEQUENCE: 23

His Ser Asp Ala Val Phe Thr Glu Asn Tyr Thr Arg Leu Arg Arg Gln
1               5                   10                  15

Leu Ala Val Arg Arg Tyr Leu
            20

<210> SEQ ID NO 24
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (30)..(30)
<223> OTHER INFORMATION: Amidation

<400> SEQUENCE: 24

His Ser Asp Ala Val Phe Thr Ala Asn Tyr Thr Arg Leu Arg Arg Gln
1               5                   10                  15

Leu Ala Val Arg Arg Tyr Leu Ala Ala Ile Leu Gly Arg Arg
            20                  25                  30

<210> SEQ ID NO 25
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (23)..(23)
<223> OTHER INFORMATION: Amidation

<400> SEQUENCE: 25

His Ser Asp Ala Val Phe Thr Ala Asn Tyr Thr Arg Leu Arg Arg Gln
1               5                   10                  15

Leu Ala Val Arg Arg Tyr Leu
            20

<210> SEQ ID NO 26
<211> LENGTH: 30
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MOD_RES
<222> LOCATION: (30)..(30)
<223> OTHER INFORMATION: Amidation

<400> SEQUENCE: 26

His Ser Asp Ala Val Phe Thr Asp Asn Tyr Thr Arg Leu Arg Arg Gln
1               5                   10                  15

Leu Ala Val Arg Arg Tyr Leu Ala Ala Val Leu Gly Arg Arg
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (30)..(30)
<223> OTHER INFORMATION: Amidation

<400> SEQUENCE: 27

His Ser Asp Ala Ile Phe Thr Asp Ser Tyr Ser Arg Tyr Arg Arg Gln
1               5                   10                  15

Leu Ala Val Arg Arg Tyr Leu Ala Ala Val Leu Gly Arg Arg
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 28

His Ser Asp Ala Ile Phe Thr Asp Ser Tyr Ser Arg Tyr Arg Arg Gln
1               5                   10                  15

Leu Ala Val Arg Arg Tyr Leu Ala Ala Ile Leu Gly Arg Arg
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (30)..(30)
<223> OTHER INFORMATION: Amidation

<400> SEQUENCE: 29

His Ser Asp Ala Ile Phe Thr Asp Ser Tyr Ser Arg Tyr Arg Arg Gln
1               5                   10                  15

Leu Ala Val Arg Arg Tyr Leu Ala Ala Val Leu Gly Arg Arg
            20                  25                  30

<210> SEQ ID NO 30
<211> LENGTH: 38
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MOD_RES
<222> LOCATION: (38)..(38)
<223> OTHER INFORMATION: Amidation

<400> SEQUENCE: 30

His Ser Asp Ala Ile Phe Thr Asp Ser Tyr Ser Arg Tyr Arg Arg Gln
1               5                   10                  15

Leu Ala Val Arg Arg Tyr Leu Ala Ala Val Leu Gly Arg Arg Tyr Arg
            20                  25                  30

Gln Arg Val Arg Asn Arg
        35

<210> SEQ ID NO 31
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (38)..(38)
<223> OTHER INFORMATION: Amidation

<400> SEQUENCE: 31

His Ser Asp Ala Ile Phe Thr Asp Ser Tyr Ser Arg Tyr Arg Arg Gln
1               5                   10                  15

Leu Ala Val Arg Arg Tyr Leu Ala Ala Ile Leu Gly Arg Arg Tyr Arg
            20                  25                  30

Gln Arg Val Arg Asn Arg
        35

<210> SEQ ID NO 32
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (23)..(23)
<223> OTHER INFORMATION: Amidation

<400> SEQUENCE: 32

His Ser Asp Ala Ile Phe Thr Asp Ser Tyr Ser Arg Tyr Arg Arg Gln
1               5                   10                  15

Leu Ala Val Arg Arg Tyr Leu
            20

<210> SEQ ID NO 33
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (23)..(23)
<223> OTHER INFORMATION: Amidation

<400> SEQUENCE: 33

His Ser Asp Ala Ile Phe Thr Asp Ser Tyr Ser Arg Tyr Arg Arg Gln
1               5                   10                  15
```

```
Leu Ala Val Arg Arg Tyr Leu
        20

<210> SEQ ID NO 34
<211> LENGTH: 23
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (23)..(23)
<223> OTHER INFORMATION: Amidation

<400> SEQUENCE: 34

His Ser Asp Gly Ile Phe Thr Asp Ser Tyr Ser Arg Tyr Arg Arg Gln
1               5                   10                  15

Leu Ala Val Arg Arg Tyr Leu
        20
```

PEPTIDES AND MEDICINAL COMPOSITIONS CONTAINING THE SAME

TECHNICAL FIELD

The present invention relates to a peptide derivative having inhibited isomerization and high stability during the production and storage of a PACAP/VIP derivate and in vivo.

BACKGROUND ART

Vasoactive intestinal peptide (VIP) is referred to as a brain-gut peptide, which is a type of biologically active peptide capable of accelerating the blood flow and lowering the blood pressure. This VIP is extracted from the porcine intestine and is comprised of 28 amino acid residues (see, for example, S. I. Said et al., Science, U.S.A., 1970, vol. 169, p. 1217). In contrast, pituitary adenylate cyclase activating polypeptide (PACAP) is a peptide being comprised of 38 amino acid residues, which was isolated from sheep hypothalamus, and the structure thereof was determined based on the bioassay system for activating adenylate cyclase in cultured pituitary cells. Two types of PACAP, i.e., PACAP38 and PACAP27, are present (see, for example, A. Miyata et al., Biochemical and biophysical research communications, U.S.A., 1989, vol. 164, p. 567). The structure of the amino acid sequence consisting of 27 amino acid residues from the N-terminus of PACAP is very similar to that of VIP. Since the amino acid sequence of VIP and that of PACAP are similar to those of secretin, glucagon, and the like, VIP and PACAP are considered to be peptides belonging to the glucagon-secretin superfamily. PACAP and VIP exhibit their biological activities via PACAP/VIP receptors. Such PACAP/VIP receptors are extensively distributed throughout the body of an organism, and therefore, PACAP/VIP is reported to have a variety of biological activities. Examples thereof include an antiasthmatic effect (JP Patent Publication (Kokai) No. 8-333276 A (1996)), a hypotensive effect (JP Patent Publication (Kokai) No. 63-179894 A (1988)), a hair-restoring effect (JP Patent Publication (Kokai) No. 1-83012 A (1989)), an effect of ameliorating male erectile dysfunction (JP Patent Publication (Kokai) No. 1-19097 A (1989)), an effect of enhancing vaginal lubrication (JP Patent Publication (Kokai) No. 1-501937 A (1989)), an effect of inhibiting the movement in the gastrointestinal tract (JP Patent Publication (Kohyo) No. 6-507415 A (1994)), an effect of ameliorating neurodegenerative diseases, hypoxia, and reduced memory skills (JP Patent Publication (Kokai) No. 7-69919 A (1995)), an effect of treating skin ulcer (JP Patent Publication (Kokai) No. 8-40926 A (1996)), acceleration of neural network construction (JP Patent Publication (Kokai) No. 2001-226284 A), and activity as an agent for ameliorating conformational diseases (Onoue S. et al., FEBS Letters, Holland, 2002, vol. 522, pp. 65-70). If such biological activities were taken into consideration, medical applications of PACAP and VIP may be very extensive. However, biologically active peptides, such as PACAP and VIP, are generally unstable, they are immediately metabolized particularly in the body of an organism, and thus, the duration of their effects is very short. Accordingly, the present inventors created a PACAP/VIP derivative possessing enzyme resistance as a novel function (JP Patent Publication (Kokai) No. 8-333276 A (1996)). They demonstrated that the PACAP/VIP derivative had excellent stability against the metabolism caused by in vivo peptidase such as trypsin (Kashimoto K. et al., Peptide Chemistry, 1996, vol. 1997, pp. 249-252), and such derivative had significant effects of prolonging drug effects by employing the effects of bronchial dilation as an indicator (Yoshihara, S. et al., Peptides, U.S.A., 1998, vol. 19, pp. 593-597; and Yoshihara, S. et al., British Journal of Pharmacology, 1997, vol. 121, pp. 1730-1734). Thus, the long-acting PACAP/VIP derivative was considered to be very useful for medical applications and it was considered to be a probable candidate as a drug targeting the aforementioned various biological and pharmacological activities. Although the biochemical stability of the PACAP/VIP derivative was confirmed, it was found that such derivative might cause serious problems in terms of pharmaceutical stability, particularly in terms of long-lasting stability in the form of a solution. Such drastic degradation gives rise to deep concern over diminished activity of PACAP/VIP, unexpected side-effects caused by impurities generated, and the like. Because of biological and pharmacological activities of PACAP/VIP, single administration of drugs comprising the same is hardly sufficient and thus, it would be easy to deduce that such drugs must be continuously administered in clinical settings over a long period of time. Therefore, generation of by-products resulting from various problems concerning stability is particularly a serious issue.

DISCLOSURE OF THE INVENTION

The present invention is directed to providing a pharmaceutical composition comprising a PACAP/VIP derivative that is highly stable and is safe for clinical use.

The present inventors have conducted concentrated studies concerning the factors that contribute to the instability of PACAP/VIP and a peptide derivative thereof in a solution. As a result, they found that isomerization occurred in some sequences and clinical use thereof as an active ingredient of a pharmaceutical composition was not preferable. Such isomerization is peculiar to acidic amino acid, such as aspartic acid or glutamic acid, and its amide forms, i.e., asparagine and glutamine. It is reported that peptides and proteins comprising such amino acids are likely to generate as a by-product succinimide or glutaric acid imide under acidic or basic conditions, depending on the structure of an adjacent amino acid (Bodanszky, M. et al., Int. J. Pept. Protein. Res., 1978, 12, 69; Nobuo Izumiya et al., "*Pepuchido Gousei no Kiso to Jikken* (*Fundamentals and Experiment of Peptide Synthesis*)," Maruzen, 71-72). This side reaction is more likely to occur when an amino acid side chain is protected with benzyl ester compared to when the side chain is free. Aspartylpeptide is particularly unstable and it may form imide under neutral conditions. A peptide becomes unstable particularly when glycine, serine, threonine, or histidine is present next to aspartic acid and asparagine. In the case of VIP, the Asn-Ser sequence at positions 24 and 25 is particularly likely to cause isomerization. Peptide 4, which is an enzyme-resistant VIP derivative, causes similar isomerization in the Asn-Gly sequence at positions 28 and 29 in addition to the Asn-Ser sequence at positions 24 and 25. According to the report of Kitada et al. (Peptide Chemistry 1990, 1991, 239-244), VIP and its relevant derivative easily form succinimide in the Asp-Asn sequence at positions 8 and 9. In the case of PACAP, the Asp-Gly sequence at positions 3 and 4 can form succinimide, and thus its stability in a solution is a serious concern.

Therefore, the present inventors focused on these sequences and have attempted to substitute these sequences with more stable amino acid sequences to produce a group of compounds having the same biological activities as PACAP/VIP peptide and having improved stability.

According to the previous report by the present inventors (Onoue, S. et al., Biomed. Res., 1999, 20, 219-231; Onoue, S. et al., Peptides, 2001, 22, 867-872; and Onoue, S. et al., Pharmacol. Rev. Commun., 2002, 12, 1-9), the N-terminal structure of PACAP/VIP significantly contributes to receptor-specific recognition properties at the time of bonding between PACAP/VIP and a PACAP/VIP receptor, which is essential for exhibiting functions thereof. Based on such concept, positions 24 and 25 constituting an instability factor sequence of VIP were substituted with positions 24 and 25 of a stable sequence of PACAP (i).

Based on the fact that Asn-28 of VIP did not contribute to activity, which had been found by the present inventors (Nagano, Y. et al., Peptide Science 2001, 2002, 147-150), position 28 of peptide 4 (a modified peptide having increased Arg content compared with wild-type VIP) was deleted to eliminate the risk of isomerization caused in the Asn-Gly sequence (ii).

Met-17 of VIP is converted into methionine sulfoxide upon immediate in vivo metabolism or during its production process and significantly influences activities. Thus, Met-17 is substituted with Leu or Nle (iii).

Also, the present inventors produced a compound derived from VIP by substituting Asp-8 with Glu or Ala, involving a lower risk of isomerization than Asp. When position 8 of VIP was substituted with Ala, its receptor binding activity was reported to improve (Igarashi, H. et al., J. Pharmacol. Exp. Ther., 2002, 37-50). Thus, stabilization and a high level of activity of the derivative are expected.

The present inventors reported that the minimal active unit of VIP was comprised of 23 residues (Nagano, Y. et al., Peptide Science 2001, 2002, 147-150). Thus, biological activity of VIP is expected to remain in a VIP derivative having the aforementioned amino acid substitution if at least 23 residues from the N terminus are retained.

In order to inhibit succinyl peptide formation at positions 3 and 4 of PACAP, the Gly-4 can be substituted with Ala which is the amino acid residue at the same position of VIP for stabilization (iv). This substitution is effective for stabilizing PACAP-associated peptides, such as peptide 3 (PACAP 38), peptide 5 (PACAP30), and peptide 6 (a modified peptide having increased Arg content compared with PACAP 38), as well as for stabilizing peptide 2 (PACAP 27).

It is already known that the minimal active unit of PACAP is comprised of 23 residues from the N-terminus, as is true in the case of VIP (Kitada, C. et al., Peptide Chemistry 1990, 1991, 239-244). Thus, the group of PACAP derivatives, if they retain at least 23 residues from the N-terminus, is expected to have biological and pharmacological effects of PACAP.

Based on such point of view, the present inventors synthesized a large variety of peptides, and then found peptides having biological activities similar to or higher than those of wild-type VIP and PACAP and having high stability.

More specifically, the present invention provides the following (1) to (12).

(1) A peptide composed of at least 23 residues from the N-terminal of the peptide represented by formula (I) or a pharmaceutically acceptable salt thereof:

(SEQ ID NO:1)
His-Ser-Asp-Ala-A-Phe-Thr-B-C-Tyr-D-Arg-E-Arg-F-

Gln-G-Ala-Val-H-I-Tyr-Leu-Ala-Ala-J-K-L  (I)

wherein A represents Val or Ile; B represents Asp, Glu, or Ala; C represents Asn or Ser; D represents Thr or Ser; E represents Leu or Tyr; F, H, and I each independently represent Lys or Arg; G represents Leu or nLeu; J represents Ile or Val; K represents Leu, Leu-Asn, Leu-Gly, Leu-Gly-Lys, Leu-Gly-Arg, Leu-Gly-Lys-Lys, Leu-Gly-Lys-Arg, Leu-Gly-Arg-Arg, Leu-Gly-Lys-Arg-Tyr-Lys-Gln-Arg-Val-Lys-Asn-Lys, or Leu-Gly-Arg-Arg-Tyr-Arg-Gln-Arg-Val-Arg-Asn-Arg; and L represents a moiety of the α-carboxyl group of the C-terminal amino acid which may be modified; i.e., —NH$_2$ or —OH.

(2) The peptide according to (1) or a pharmaceutically acceptable salt thereof, which consists of 23 amino acid residues from the N terminus of the peptide represented by formula (I), wherein A represents Val; B represents Asp; C represents Asn; D represents Thr; E represents Leu; F, H, and I each independently represent Arg; G represents Leu; and L represents —NH$_2$. Specifically, such peptide is equivalent to peptide 10 (SEQ ID NO: 11).

(3) The peptide according to (1) or a pharmaceutically acceptable salt thereof, wherein, in formula (I), A represents Val; B represents Asp; C represents Asn; D represents Thr; E represents Leu; F, H, and I each independently represent Arg; G represents Leu; J represents Ile; K represents Leu-Gly-Arg-Arg; and L represents —NH$_2$. Specifically, such peptide is equivalent to peptide 12 (SEQ ID NO: 13).

(4) The peptide according to (1) or a pharmaceutically acceptable salt thereof, wherein, in formula (I), A represents Val; B represents Glu; C represents Asn; D represents Thr; E represents Leu; F, H, and I each independently represent Arg; G represents Leu; J represents Ile; K represents Leu-Gly-Arg-Arg; and L represents —NH$_2$. Specifically, such peptide is equivalent to peptide 21 (SEQ ID NO: 22).

(5) The peptide according to (1) or a pharmaceutically acceptable salt thereof, wherein, in formula (I), A represents Val; B represents Ala; C represents Asn; D represents Thr; E represents Leu; F, H, and I each independently represent Arg; G represents Leu; J represents Ile; K represents Leu-Gly-Arg-Arg; and L represents —NH$_2$. Specifically, such peptide is equivalent to peptide 23 (SEQ ID NO: 24).

(6) The peptide according to (1) or a pharmaceutically acceptable salt thereof, wherein, in formula (I), A represents Val; B represents Asp; C represents Asn; D represents Thr; E represents Leu; F, H, and I each independently represent Arg; G represents Leu; J represents Val; K represents Leu-Gly-Arg-Arg; and L represents —NH$_2$. Specifically, such peptide is equivalent to peptide 25 (SEQ ID NO: 26).

(7) The peptide according to (1) or a pharmaceutically acceptable salt thereof, wherein, in formula (I), A represents Ile; B represents Asp; C represents Ser; D represents Ser; E represents Tyr; F, H, and I each independently represent Arg; G represents Leu; J represents Val; K represents Leu-Gly-Arg-Arg; and L represents —NH$_2$. Specifically, such peptide is equivalent to peptide 26 (SEQ ID NO: 27).

(8) The peptide according to (1) or a pharmaceutically acceptable salt thereof, wherein, in formula (I), A represents Ile; B represents Asp; C represents Ser; D represents Ser; E represents Tyr; F, H, and I each independently represent Arg; G represents Leu; J represents Val; K represents Leu-Gly-Arg-Arg-Tyr-Arg-Gln-Arg-Val-Arg-Asn-Arg; and L represents —NH$_2$. Specifically, such peptide is equivalent to peptide 29 (SEQ ID NO: 30).

(9) The peptide according to (1) or a pharmaceutically acceptable salt thereof, which consists of 23 amino acid residues from the N terminus of the peptide represented by formula (I), wherein A represents Ile; B represents Asp; C represents Ser; D represents Ser; E represents Tyr; F, H, and I each independently represent Arg; G represents Leu; and L represents —NH₂. Specifically, such peptide is equivalent to peptide 31 (SEQ ID NO: 32).

Peptides 10, 12, 21, 23, 25, 26, 29, and 31 are modified peptides to which the aforementioned modifications (i) to (iv) have been applied. Further, amino acids at positions 8 of peptides 21 and 23 have been altered to Glu or Ala.

(10) A pharmaceutical composition comprising the peptide according to any one of (1) to (9) or a pharmaceutically acceptable salt thereof.

(11) The pharmaceutical composition according to (10), which comprises the peptide according to any one of (1) to (9) or a pharmaceutically acceptable salt thereof in an amount of at least 50% by weight based on the entire biologically active peptide as an active ingredient.

The term "active ingredient" refers to a substance being contained in the pharmaceutical composition and having effects of treating, preventing, altering, or alleviating a disease, symptoms, or conditions of a subject. The term "biologically active peptide" refers to a peptide having biological activity on the subject. In the present description, such peptides include PACAP/VIP peptide, a salt thereof, and a derivative thereof. "PACAP/VIP peptides" include wild-type PACAP or VIP of humans and animals, a peptide having the amino acid sequence similar to that of PACAP or VIP, and a peptide having biological activity similar to that of PACAP or VIP. Additionally, "PACAP/VIP peptides" include a peptide belonging to the glucagon-secretin family.

(12) The pharmaceutical composition according to (10) or (11) for treating or preventing one or more diseases or symptoms selected from the group consisting of ischemic cerebrovascular disorders including cerebral embolism and cerebral thrombosis, diseases causing toxicity to the central or peripheral nervous system, cerebrovascular ischemia, thrombosis, conformational diseases, neurodegenerative diseases, hair loss, erectile dysfunction, dementia, kidney failure, optic nerve degenerative diseases including atrophy of optic nerve and ischemic optic neuropathy, and retinal degenerative diseases, for improving blood flow, for relaxing the bronchial smooth muscle, or for inhibiting the movement in the gastrointestinal tract.

Hereafter, the present invention is described in detail.

Specifically, the highly stable peptide derivative according to the present invention consists of the amino acid sequence represented by formula (I). Representative examples of such peptides are shown in Table 1. Peptides 10 to 32 shown therein are equivalent to sequences shown in SEQ ID NOs: 11 to 33 of the Sequence Listing. Peptides 10, 22, 24, 31, and 32 are peptides corresponding to regions consisting of 23 residues from the N-terminus, peptides 13, 28, and 32 each independently have an acetyl group bound to the N-terminal amino group, and peptide 14 has a stearyl group bound to its N-terminal amino group. Peptide 33 (SEQ ID NO: 34) consists of 23 residues having the same amino acid sequence as peptide 31 (SEQ ID NO: 32), except that the amino acid at position 4 is glycine.

TABLE 1

| Peptide No. | A | B | C | D | E | F | G | H | I | J | K | L |
|---|---|---|---|---|---|---|---|---|---|---|---|---|
| 10 | Val | Asp | Asn | Thr | Leu | Arg | Leu | Arg | Arg | | | NH₂ |
| 11 | Val | Asp | Asn | Thr | Leu | Lys | Leu | Lys | Lys | Ile | Leu-Asn | NH₂ |
| 12 | Val | Asp | Asn | Thr | Leu | Arg | Leu | Arg | Arg | Ile | Leu-Gly-Arg-Arg | NH₂ |
| 13 | Val | Asp | Asn | Thr | Leu | Arg | Leu | Arg | Arg | Ile | Leu-Gly-Arg-Arg | NH₂ |
| 14 | Val | Asp | Asn | Thr | Leu | Arg | Leu | Arg | Arg | Ile | Leu-Gly-Arg-Arg | NH₂ |
| 15 | Val | Asp | Asn | Thr | Leu | Arg | Leu | Arg | Arg | Ile | Leu-Gly-Arg-Arg | OH |
| 16 | Val | Asp | Asn | Thr | Leu | Arg | Nle | Arg | Arg | Ile | Leu-Gly-Arg-Arg | NH₂ |
| 17 | Val | Asp | Asn | Thr | Leu | Arg | Leu | Arg | Arg | Ile | Leu-Gly | NH₂ |
| 18 | Val | Asp | Asn | Thr | Leu | Arg | Leu | Arg | Arg | Ile | Leu-Gly-Lys | NH₂ |
| 19 | Val | Asp | Asn | Thr | Leu | Arg | Leu | Arg | Arg | Ile | Leu-Gly-Arg | NH₂ |
| 20 | Val | Asp | Asn | Thr | Leu | Arg | Leu | Arg | Arg | Ile | Leu-Gly-Lys-Arg | NH₂ |
| 21 | Val | Glu | Asn | Thr | Leu | Arg | Leu | Arg | Arg | Ile | Leu-Gly-Arg-Arg | NH₂ |
| 22 | Val | Glu | Asn | Thr | Leu | Arg | Leu | Arg | Arg | | | NH₂ |
| 23 | Val | Ala | Asn | Thr | Leu | Arg | Leu | Arg | Arg | Ile | Leu-Gly-Arg-Arg | NH₂ |
| 24 | Val | Ala | Asn | Thr | Leu | Arg | Leu | Arg | Arg | | | NH₂ |
| 25 | Val | Asp | Asn | Thr | Leu | Arg | Leu | Arg | Arg | Val | Leu-Gly-Arg-Arg | NH₂ |
| 26 | Ile | Asp | Ser | Ser | Tyr | Arg | Leu | Arg | Arg | Val | Leu-Gly-Arg-Arg | NH₂ |
| 27 | Ile | Asp | Ser | Ser | Tyr | Arg | Leu | Arg | Arg | Ile | Leu-Gly-Arg-Arg | NH₂ |
| 28 | Ile | Asp | Ser | Ser | Tyr | Arg | Leu | Arg | Arg | Val | Leu-Gly-Arg-Arg | NH₂ |
| 29 | Ile | Asp | Ser | Ser | Tyr | Arg | Leu | Arg | Arg | Val | Leu-Gly-Arg-Arg-Tyr-Arg-Gln-Arg-Val-Arg-Asn-Arg | NH₂ |
| 30 | Ile | Asp | Ser | Ser | Tyr | Arg | Leu | Arg | Arg | Ile | Leu-Gly-Arg-Arg-Tyr-Arg-Gln-Arg-Val-Arg-Asn-Arg | NH₂ |
| 31 | Ile | Asp | Ser | Ser | Tyr | Arg | Leu | Arg | Arg | | | NH₂ |
| 32 | Ile | Asp | Ser | Ser | Tyr | Arg | Leu | Arg | Arg | | | NH₂ |
| 33 | Ile | Asp | Ser | Ser | Tyr | Arg | Leu | Arg | Arg | | | NH₂ |

When the above peptides are used, a polar or non-polar substance (e.g., fatty acid or acyl) can be bound to the N-terminus thereof to alter the molecular polarity, or a polymeric compound such as polyethylene glycol or glucosaminoglycan (hyaluronic acid) can be bound thereto to enhance enzyme resistance. Such a peptide can be bound to a liposome support to be encapsulated into the liposome, or they can be immobilized on the surface of a lipid membrane. A person skilled in the art knows that introduction of an acyl group can result in inhibition of self-aggregation as well as improvement of activity.

The peptide according to the present invention was found to be very stable in an aqueous solution such as distilled water or a buffer. When the peptide according to the present invention is stored in a solution at pH levels of 6.0 and 7.0 at 40° C. for 1 week, for example, the peptide can be preserved with a rate of 70% or higher, preferably 80% or higher, and more preferably 85% or higher. When the peptide is stored in a solution adjusted at pH levels of 6.0 and 7.0 at 55° C. for 3 days, it can be preserved with a rate of 85% or higher and preferably 90% or higher. In the present invention, peptides 10, 12, 21, 23, 25, 26, 29, and 31 are particularly preferable.

The peptide used for the neurite inducer according to the present invention is not particularly limited, and it can be synthesized in accordance with a conventional technique of peptide synthesis. Such peptide can be synthesized in accordance with the method described in, for example, "The Peptides," vol. 1, 1966, Schreder and Luhke, Academic press, New York, U.S.A. or "Pepuchido Gousei (Peptide Synthesis)," Izumiya et al., Maruzen, 1975. More specifically, peptide synthesis can be carried out via a variety of techniques, such as the azide method, the acid chloride method, the acid anhydride method, the mixed anhydride method, the DCC method, the active ester methods (e.g., the p-nitrophenyl ester method, N-hydroxysuccinic imide ester method, or the cyanomethyl ester method), the method involving the use of Woodward reagent K, the carboimidazole method, the oxidation-reduction method, and the DCC-additive (HONB, HOBt, or HOSu) method. These techniques can be applied to solid phase synthesis and liquid phase synthesis.

In the present invention, peptide synthesis is carried out in accordance with generalized techniques for polypeptide synthesis as mentioned above. For example, peptide synthesis is carried out via what is called a stepwise method in which amino acids are sequentially fused to the terminal amino acid residue one-by-one. Alternatively, amino acids are divided into several fragments, and the fragments are coupled to each other.

A specific example of a method for stepwise solid phase peptide synthesis is the method of Merrifield, R. B. (Solid phase peptide synthesis, J. Amer. Chem. Soc., 85, 2149-2159, 1963), and it can be carried out in the following manner. The C-terminal amino acid (a protected amino group) is first bound to insoluble resin via its carboxyl group, and the amino-protecting group of the C-terminal amino acid is then removed. Subsequently, a reactive carboxyl group of an amino group-protected amino acid is sequentially fused to the resulting free reactive amino group in accordance with the amino acid sequence of the target peptide. Thus, a total sequence is synthesized in a stepwise manner and the peptide is then separated from insoluble resin.

Any insoluble resin can be employed for the solid phase peptide synthesis, as long as it can bind to a reactive carboxyl group. Examples thereof include benzhydrylamine (BHA) resin, chloromethyl resin, oxymethyl resin, aminomethyl resin, methylbenzhydrylamine (MBHA) resin, 4-aminomethylphenoxymethyl resin, 4-hydroxymethylphenoxymethyl resin, and 4-oxymethylphenylacetamidemethyl resin.

When a 9-fluorenylmethyloxycarbonyl (Fmoc) group is used as an α-amino-protecting group, for example, use of 4-hydroxymethylphenoxymethyl resin, from which a peptide can be eliminated with the aid of trifluoroacetic acid (TFA), is preferable. When a t-butoxycarbonyl (Boc) group is used, for example, use of 4-oxymethylphenylacetamidemethyl (PAM) resin, from which a peptide can be eliminated with the aid of hydrogen fluoride, is preferable. The amount of peptide is preferably 0.5 mmole or lower per g of resin.

The method described above requires bonding of a protecting group to an amino group involved with peptide bond of amino acids, elimination of the protecting group, and activation of a carboxyl group involved with the peptide bond of amino acids.

Examples of amino-protecting groups include groups such as benzyloxycarbonyl (Z), t-butoxycarbonyl (Boc), t-amyloxycarbonyl (Aoc), isobornyloxycarbonyl, p-methoxybenzyloxycarbonyl, 2-chloro-benzyloxycarbonyl, adamantyloxycarbonyl, trifluoroacetyl, phthaloyl, formyl, o-nitrophenylsulfenyl, and diphenylphosphinothioyl.

Side chain functional groups of amino acids, such as His, Tyr, Thr, Lys, Asp, Arg, and Ser, are preferably protected. A functional group can be protected in accordance with a conventional technique in which a common protecting group listed below is bound to the functional group. After the completion of the reaction, the protecting group is eliminated.

Examples of imino-protecting groups of His include benzyloxymethyl (Bom), p-toluenesulfonyl (Tos), benzyl (Bzl), benzyloxycarbonyl (Z), and trityl groups.

The hydroxyl group of Ser and of Thr can be protected via, for example, esterification or etherification, although such protection is not essential. Examples of groups that are suitable for esterification include lower alkanoyl groups such as acetyl, aroyl groups such as benzoyl, and groups derived from carbonic acids such as benzoyloxycarbonyl and ethyloxycarbonyl. Examples of groups that are suitable for etherification include benzyl (Bzl), tetrahydropyranyl, and tert-butyl groups.

Examples of protecting groups for hydroxyl groups of Tyr include benzyl (Bzl), bromobenzyloxycarbonyl (Br-Z), dichlorobenzyl ($Cl_2$-Bzl), benzyloxycarbonyl (Z), acetyl, and p-toluenesulfonyl (Tos) groups.

Examples of protecting groups for amino groups of Lys include benzyloxycarbonyl (Z), chlorobenzyloxycarbonyl (Cl-Z), dichlorobenzyl ($Cl_2$-Bzl), t-butoxycarbonyl (Boc), and p-toluenesulfonyl (Tos) groups.

Examples of protecting groups for guanidino groups of Arg include p-toluenesulfonyl (Tos), nitro, benzyloxycarbonyl (Z), and t-amyloxycarbonyl (Aoc) groups.

A carboxyl group of Asp is protected via, for example, esterification with the aid of benzyl alcohol, methanol, ethanol, tert-butanol, and cyclohexyl (cHex).

Examples of protecting groups for other amino acids, such as an indolyl group of Trp, include formyl, carbobenzoxyl, 4-methoxy-2,3,6-trimethylbenzenesulfonyl, and 2,2,2-trichloroethyloxycarbonyl, although such protection is not essential.

A method to protect a thiomethyl group of Met includes previously preparing a methyl sulfoxide and then reducing it, although such method is not essential.

In contrast, a carboxyl group can be activated in accordance with a conventional technique, and known reagents and the like can be adequately selected for activation. For example, a carboxyl group can be activated by allowing the carboxyl group to react with a variety of reagents to form relevant acid chloride, acid anhydride or mixed anhydride, azide, or active esters (e.g., esters with pentachlorophenol, p-nitrophenol, N-hydroxysuccinic acid imide, N-hydroxybenzotriazole, or N-hydroxy-5-norbornene-2,3-dicarboxyimide).

Any solvent that can be used for peptide bond formation can be used for condensation reaction (peptide bond formation) between a reactive amino group and a reactive carboxyl group in the solid phase synthesis. For example, anhydrous or hydrous dimethylformamide (DMF), dimethylsulfoxide (DMSO), pyridine, chloroform, dioxane, dichloromethan (DCM), tetrahydrofuran (THF), ethyl acetate, N-methyl pyrrolidone, or hexamethylphosphoric triamide (HMPA) can be used solely or in combinations of 2 or more.

The aforementioned condensation reaction can be carried out in the presence of a condensing agent, such as carbodiimide reagents such as dicyclohexylcarboxyimide (DCC) or carbodiimidazole, tetraethyl pyrophosphate, and benzotriazole-N-hydroxy-tris-dimethylamino-phosphonium hexafluorophosphate (a Bop reagent).

The synthesized peptide can be subjected to desalting and purification in accordance with common techniques. Examples of common techniques include ion-exchange chromatography on DEAE-cellulose, partition chromatography on Sephadex LH-20 or Sephadex G-25, normal phase chromatography on silica gel, reverse phase chromatography on ODS-silica gel, and high-performance liquid chromatography.

The thus purified peptide can be converted into a form of pharmacologically acceptable salt, such as acetate, hydrochloride, or phosphate, using various types of acids according to need.

The peptide or a salt thereof is prepared as a pharmaceutical composition in the form of liquid, injection, tablet, powder, granule, suppository, enteric-coated tablet, nasal drop, inhalation formulation, buccal formulation, capsule, eye drop, ointment, percutaneous formulation, sustained-release agent, and other drug delivery systems using a pharmaceutically acceptable solvent, excipient, carrier, or adjuvant in accordance with conventional techniques for producing pharmaceutical preparations.

The peptide according to the present invention or a salt thereof has biological activity that is the same as that of known PACAP/VIP, and it can be used in the same manner. The peptide and a salt thereof are capable of inducing neurite formation and thus are useful as neurite inducers. Such agents are particularly effective for preventing and treating various diseases involving nerve cell degeneration, such as Alzheimer's dementia, Parkinson's disease, nerve cell death, neuroblastoma, or amnesia. In addition, the peptide and a salt thereof are effective for defense against drugs that are hazardous to the nervous system. Further, they are also useful as an antiasthmatic agent, due to the effect of the peptide in dilating the bronchi, and as an inhibitor of gastric peristaltic movement during endoscopy. As with the case of PACAP/VIP, a pharmaceutical composition comprising the peptide according to the present invention or a salt thereof can also be used for treating or preventing one or more diseases or symptoms selected from the group consisting of ischemic cerebrovascular disorders including cerebral embolism and cerebral thrombosis, cranial or peripheral nerve deficits resulting from the aforementioned ischemic disorders or other sources, conformational diseases, neurodegenerative diseases, hair loss, erectile dysfunction, dementia, kidney failure, optic nerve degenerative diseases including atrophy of optic nerve and ischemic optic neuropathy, and retinal degenerative diseases. Such pharmaceutical composition can also be used for improving blood flow, for relaxing the bronchial smooth muscle, or for inhibiting the movement in the gastrointestinal tract, although applications thereof are not limited thereto. It should be noted that the present inventors have already discovered that the PACAP/VIP peptide is capable of protecting nerves against a specific protein that could result in conformational disease (Japanese Patent Application No. 2001-386699).

The pharmaceutical composition according to the present invention can be safely administered to mammalians such as humans, mice, rats, rabbits, dogs, or cats parenterally or orally or via a drug delivery system such as nasal drops, an inhalant, a sustained-release agent, eye drops, an ointment, a percutaneous formulation, or a buccal formulation, according to need. The adequate route of administration, dosage form, dosage frequency, and other conditions can be determined by a specialist such as a physician, in accordance with the type of disease, expected effects, and general conditions of the patient. Examples of devices for administration include, but are not limited to, nasal drops, such as Jetlizer, Puvlizer, and a nasal insufflator, and inhalants, such as Spinhaler, E-haler, FlowCaps, Jethaler, Diskhaler, Rotahaler, Turbuhaler, Easyhaler, Accuhaler, Clickhaler, Inspir-Ease, and Inhalation Aid. The dose of the pharmaceutical composition can be adequately changed in accordance with the dosage form, the route of administration, conditions, and other factors. When the composition is administered to mammals including humans, for example, the peptide is administered to a patient in amounts of about 1 pg to 1 mg per kg of body weight per day. In such a case, the peptide according to the present invention or a salt thereof constitutes 50% by weight or more, preferably 80% by weight or more, and more preferably 95% by weight or more, of biologically active peptide as an active ingredient of the composition. This indicates that the amount of biologically active peptide that is not represented by formula (I) in the composition is 50% by weight or less, preferably 20% by weight or less, and particularly preferably 5% by weight or less.

This description includes part or all of the contents as disclosed in the description and/or drawings of Japanese Patent Application No. 2002-344523, which is a priority document of the present application.

PREFERRED EMBODIMENTS OF THE INVENTION

Figure 1:
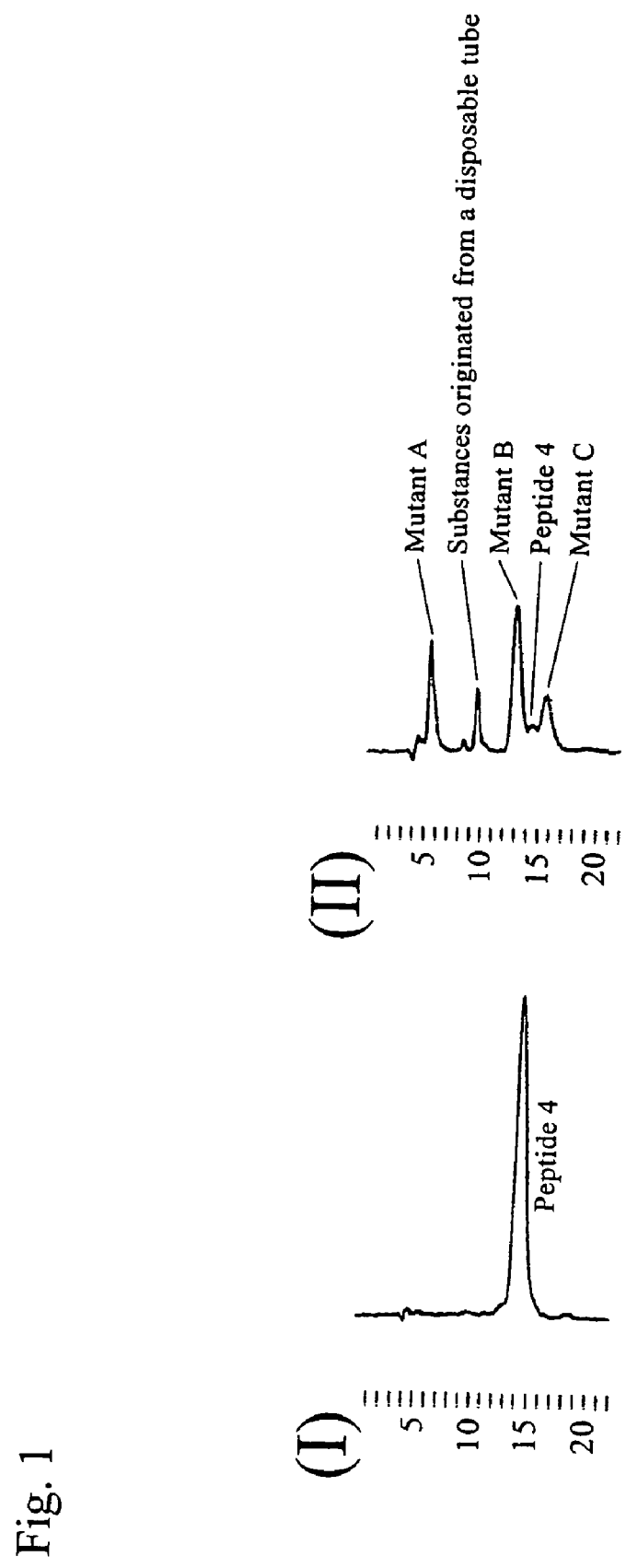
FIG. 1 is a chromatograph showing peptide 4 (I) and sample (II), which is prepared by dissolving peptide 4 in a phosphate buffer at pH 7.0 (concentration: 300 µg/ml) and allowing the solution to stand in an incubator at 55° C. for 24 hours.

The present invention is hereafter described in greater detail with reference to Examples, although the technical scope of the present invention is not limited thereto.

EXAMPLE 1

Peptide Synthesis

Peptide 12 having the amino acid sequence as shown in SEQ ID NO: 13 was produced in accordance with a conventional technique of solid phase peptide synthesis.

The MBHA.HCl resin (a polystyrene-divinylbenzene (1%) copolymer, 100 to 200 mesh) was added to a manual synthesis reaction vessel (made of glass; ϕ 6.0×29.5 cm), the resin was washed with methanol in amounts 2 to 3 times that thereof while stirring, and the washed resin was then allowed to swell via washing with dichloromethane (in amounts 2 to 3 times that of the resin) while stirring. Neutralization was carried out in 10% triethylamine/dichloromethane, Boc-Arg (Tos)-OH corresponding to the C-terminal amino acid was used in amounts equivalent to about 2 times that of the resin, and dicyclohexylcarbodiimide and N-hydroxybenzotriazole were added to perform condensation reaction. After the reaction had been carried out for about 2 hours (while stirring), the resin was washed with methanol and dichloromethane, disappearance of an α-amino group was confirmed by the Kaiser test, and deprotection was then carried out by treating the resin with 50% trifluoroacetic acid/dichloromethane for 30 minutes. Subsequently, neutralization was carried out in 10% triethylamine/dichloromethane, washing was performed again with methanol and with dichloromethane, and the Kaiser test was carried out again in order to confirm the deprotection. After the confirmation, the same procedure was repeated for coupling of Boc-Arg (Tos)-OH located at the second position from the C-terminus. Thereafter, Boc-Gly-OH, Boc-Leu-OH, Boc-Ile-OH, Boc-Ala-OH, Boc-Ala-OH, Boc-Leu-OH, Boc-Tyr (Cl$_2$-Bzl)-OH, Boc-Arg (Tos)-OH, Boc-Arg (Tos)-OH, Boc-Val-OH, Boc-Ala-OH, Boc-Leu-OH, Boc-Gln (Xan)-OH, Boc-Arg (Tos)-OH, Boc-Arg (Tos)-OH, Boc-Leu-OH, Boc-Arg (Tos)-OH, Boc-Thr (Bzl)-OH, Boc-Tyr (Cl$_2$-Bzl)-OH, Boc-Asn (Xan)-OH, Boc-Asp (OcHex)-OH, Boc-Thr (Bzl)-OH, Boc-Phe-OH, Boc-Val-OH, Boc-Ala-OH, Boc-Asp (OcHex)-OH, Boc-Ser (Bzl)-OH, and Boc-His (Bom)-OH were sequentially subjected to coupling and deprotection in that order to obtain a protected peptide corresponding to peptide 12: His (Bom)-Ser (Bzl)-Asp (OcHex)-Ala-Val-Phe-Thr (Bzl)-Asp (OcHex)-Asn-Tyr (Cl$_2$-Bzl)-Thr (Bzl)-Arg (Tos)-Leu-Arg (Tos)-Arg (Tos)-Gln-Leu-Ala-Val-Arg (Tos)-Arg (Tos)-Tyr (Cl$_2$-Bzl)-Leu-Ala-Ala-Ile-Leu-Gly-Arg-Arg-MBHA. Anhydrous hydrogen fluoride was added to the protected peptide-MBHA resin and they were allowed to react with each other in the presence of ethanedithiol and anisole. After the reaction, anhydrous hydrogen fluoride was removed by distillation under the reduced pressure, the residue was washed with ether, and 10% acetic acid was added thereto to extract peptides. The extract was purified via reverse phase column chromatography and lyophilized to obtain peptide 12.

The following peptides 1 to 33 were chemically synthesized in the same manner as described above.

Peptide 1 (SEQ ID NO:2):
His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ Peptide 2 (SEQ ID NO:3):
His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-NH$_2$ Peptide 3 (SEQ ID NO:4):
His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$ Peptide 4 (SEQ ID NO:5):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Asn-Ser-Ile-Leu-Asn-Gly-Arg-Arg-NH$_2$ Peptide 5 (SEQ ID NO:6):
His-Ser-Asp-Gly-Ile-Phe-Thr-Asp-Ser-Tyr-Ser-Arg-Tyr-Arg-Arg-Gln-Leu-Ala-Val-Arg-Arg-Tyr-Leu-Ala-Ala-Val-Leu-Gly-Arg-Arg-NH$_2$ Peptide 6 (SEQ ID NO:7):
His-Ser-Asp-Gly-Ile-Phe-Thr-Asp-Ser-Tyr-Ser-Arg-Tyr-Arg-Arg-Gln-Leu-Ala-Val-Arg-Arg-Tyr-Leu-Ala-Ala-Val-Leu-Gly-Arg-Arg-Tyr-Arg-Gln-Arg-Val-Arg-Asn-Arg-NH$_2$ Peptide 7 (SEQ ID NO:8):
His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-NH$_2$ Peptide 8 (SEQ ID NO:9):
His-Ser-Asp-Ala-Val-Phe-Thr-Asp-Asn-Tyr-Thr-Arg-Leu-Arg-Lys-Gln-Met(O)-Ala-Val-Lys-Lys-Tyr-Leu-Asn-Ser-NH$_2$ Peptide 9 (SEQ ID NO:10):
His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-NH$_2$ Peptide 10 (SEQ ID NO:11):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-NH$_2$ Peptide 11 (SEQ ID NO:12):
His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Ala-Ala-Ile-Leu-Asn-NH$_2$ Peptide 12 (SEQ ID NO:13):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Arg-Arg-NH$_2$ Peptide 13 (SEQ ID NO:14):
Acetyl-His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Arg-Arg-NH$_2$ Peptide 14 (SEQ ID NO:15):
Stearyl-His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Arg-Arg-NH$_2$ -continued Peptide 15 (SEQ ID NO:16):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Arg-Arg-OH Peptide 16 (SEQ ID NO:17):
His-Ser-Asp-Ala-Val-Phe-Thr-Asp-Asn-Tyr-Thr-Arg-Leu-Arg-Arg-Gln-Nle-Ala-Val-Arg-Arg-Tyr-Leu-Ala-Ala-Ile-Leu-Gly-Arg-Arg-NH$_2$ Peptide 17 (SEQ ID NO:18):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-NH$_2$ Peptide 18 (SEQ ID NO:19):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Lys-NH$_2$ Peptide 19 (SEQ ID NO:20):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Arg-NH$_2$ Peptide 20 (SEQ ID NO:21):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Ile-Leu-Gly-Lys-Arg-NH$_2$ Peptide 21 (SEQ ID NO:22):
His-Ser-Asp-Ala-Val-Phe-Thr-Glu-Asn-Tyr-Thr-Arg-Leu-Arg-Arg-Gln-Leu-Ala-Val-Arg-Arg-Tyr-Leu-Ala-Ala-Ile-Leu-Gly-Arg-Arg-NH$_2$ Peptide 22 (SEQ ID NO:23):
His-Ser-Asp-Ala-Val-Phe-Thr-Glu-Asn-Tyr-Thr-Arg-Leu-Arg-Arg-Gln-Leu-Ala-Val-Arg-Arg-Tyr-Leu-NH$_2$ Peptide 23 (SEQ ID NO:24):
His-Ser-Asp-Ala-Val-Phe-Thr-Ala-Asn-Tyr-Thr-Arg-Leu-Arg-Arg-Gln-Leu-Ala-Val-Arg-Arg-Tyr-Leu-Ala-Ala-Ile-Leu-Gly-Arg-Arg-NH$_2$ Peptide 24 (SEQ ID NO:25):
His-Ser-Asp-Ala-Val-Phe-Thr-Ala-Asn-Tyr-Thr-Arg-Leu-Arg-Arg-Gln-Leu-Ala-Val-Arg-Arg-Tyr-Leu-NH$_2$ Peptide 25 (SEQ ID NO:26):
His-Ser-Asp-Ala-Val-Phe-Thr-Asp-Asn-Tyr-Thr-Arg-Leu-Arg-Arg-Gln-Leu-Ala-Val-Arg-Arg-Tyr-Leu-Ala-Ala-Val-Leu-Gly-Arg-Arg-NH$_2$ Peptide 26 (SEQ ID NO:27):
His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-Ala-Ala-Val-Leu-Gly-Arg-Arg-NH$_2$ Peptide 27 (SEQ ID NO:28):
His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-Ala-Ala-Ile-Leu-Gly-Arg-Arg-NH$_2$ Peptide 28 (SEQ ID NO:29):
Acetyl-His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-Ala-Ala-Val-Leu-Gly-Arg-Arg-NH$_2$ Peptide 29 (SEQ ID NO:30):
His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-Ala-Ala-Val-Leu-Gly-Arg-Arg-Tyr-Arg-Gln-Arg-Val-Arg-Asn-Arg-NH$_2$ Peptide 30 (SEQ ID NO:31):
His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-Ala-Ala-Ile-Leu-Gly-Arg-Arg-Tyr-Arg-Gln-Arg-Val-Arg-Asn-Arg-NH$_2$ Peptide 31 (SEQ ID NO:32):
His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-NH$_2$ Peptide 32 (SEQ ID NO:33):
Acetyl-His-Ser-Asp-Ala-Ile-Phe-Thr-Asp-Ser-Tyr-Ser-Arg-Tyr-Arg-Arg-Gln-Leu-Ala-Val-Arg-Arg-Tyr-Leu-NH$_2$ Peptide 33 (SEQ ID NO:34):
His-Ser-Asp-Gly-Ile-Phe-Thr-Asp-Ser-Tyr-Ser-Arg-Tyr-Arg-Arg-Gln-Leu-Ala-Val-Arg-Arg-Tyr-Leu-NH$_2$

EXAMPLE 2

Stability of Peptide 4

Peptide 4, a modified peptide, having a higher Arg content than wild-type VIP was weighed and fractionated to about 1 mg, the fractions were dissolved in distilled water adjusted to pH levels of 4.0, 5.0, 6.0, and 7.0 (Otsuka Distilled Water), and the final concentration was adjusted to 10 μg/ml. The resulting solutions were allowed to stand in an incubator at 40° C. (LH20-11M, Nagano Kagaku) for 24 hours, analysis was carried out via reverse phase HPLC (wavelength: 220 nm; mobile phase: 28% acetonitrile/0.1% trifluoroacetic acid; column: ODS-120T (Tosoh); column temperature: 25° C.), and the amount of remaining peptide 4 was examined. As shown in Table 2, peptide degradation was significant at around the neutral pH region.

TABLE 2

| pH | Amount of remaining peptide |
|---|---|
| 4.0 | 91% |
| 5.0 | 90% |

TABLE 2-continued

| pH | Amount of remaining peptide |
|---|---|
| 6.0 | 93% |
| 7.0 | 84% |

EXAMPLE 3

Amino Acid and LC-MS Analysis of Mutant Peptide 4

Peptide 4 was dissolved in a phosphate buffer (pH: 7.0; concentration: 300 µg/ml) and allowed to stand in an incubator at 55° C. for 24 hours. A chromatograph as shown in FIG. 1 (II) was obtained. FIG. 1 (I) is a chart showing peptide 4 (the control). Mutants A and B were fractionated by HPLC and then subjected to amino acid analysis. The results of amino acid analysis of mutants were at substantially the same levels as the theoretical values for peptide 4, as shown in Table 3.

TABLE 3

| Amino acid | Peptide 4 (Theoretical value) | Mutant A | Mutant B | Mutant C |
|---|---|---|---|---|
| Asx | 5 | 5.04 | 5.06 | 5.00 |
| Thr | 2 | 2.02 | 2.02 | 2.02 |
| Ser | 2 | 1.92 | 1.84 | 2.01 |
| Glx | 1 | 1.20 | 1.11 | 1.24 |
| Gly | 1 | 1.13 | 1.04 | 1.15 |
| Ala | 2 | 2.00 | 2.00 | 2.00 |
| Val | 2 | 2.01 | 1.94 | 2.07 |
| Ile | 1 | 0.97 | 0.97 | 0.96 |
| Leu | 4 | 4.14 | 4.17 | 4.09 |
| Tyr | 2 | 2.00 | 2.09 | 1.97 |
| Phe | 1 | 1.02 | 1.00 | 1.01 |
| His | 1 | 1.35 | 1.11 | 1.40 |
| Arg | 7 | 6.98 | 6.94 | 6.91 |

The results suggest that the amino acid sequences of the mutants were very similar to that of peptide 4, and only acidic amino acids Asx and Glx may differ therefrom.

Further, the molecular weights of these mutants were measured via LC-MS, and the results as shown in Table 4 were obtained.

TABLE 4

| Specimen | Predicted molecular weight |
|---|---|
| Peptide 4 | 3761 |
| Mutant A | 3762 |
| Mutant B | 3762 |
| Mutant C | 3762 |

The results shown in Table 4 demonstrate that the molecular weights of all the mutants were increased from that of peptide 4 by 1. This suggests that Asn was altered to become Asp or Gln was altered to become Glu if the results of amino acid analysis were taken into consideration. Based on the amino acid sequence of peptide 4, it was deduced that succinimide was formed in the Asn-containing region, an amino residue was removed along therewith, and thus the molecular weight was increased by 1. Accordingly, it was confirmed that α-ω transpeptidation had occurred in the Asn-Ser sequence at positions 24 and 25 or in the Asn-Gly sequence at positions 28 and 29 in peptide 4.

EXAMPLE 4

Structures of Peptide 7 and Peptide 8

Figure 2:
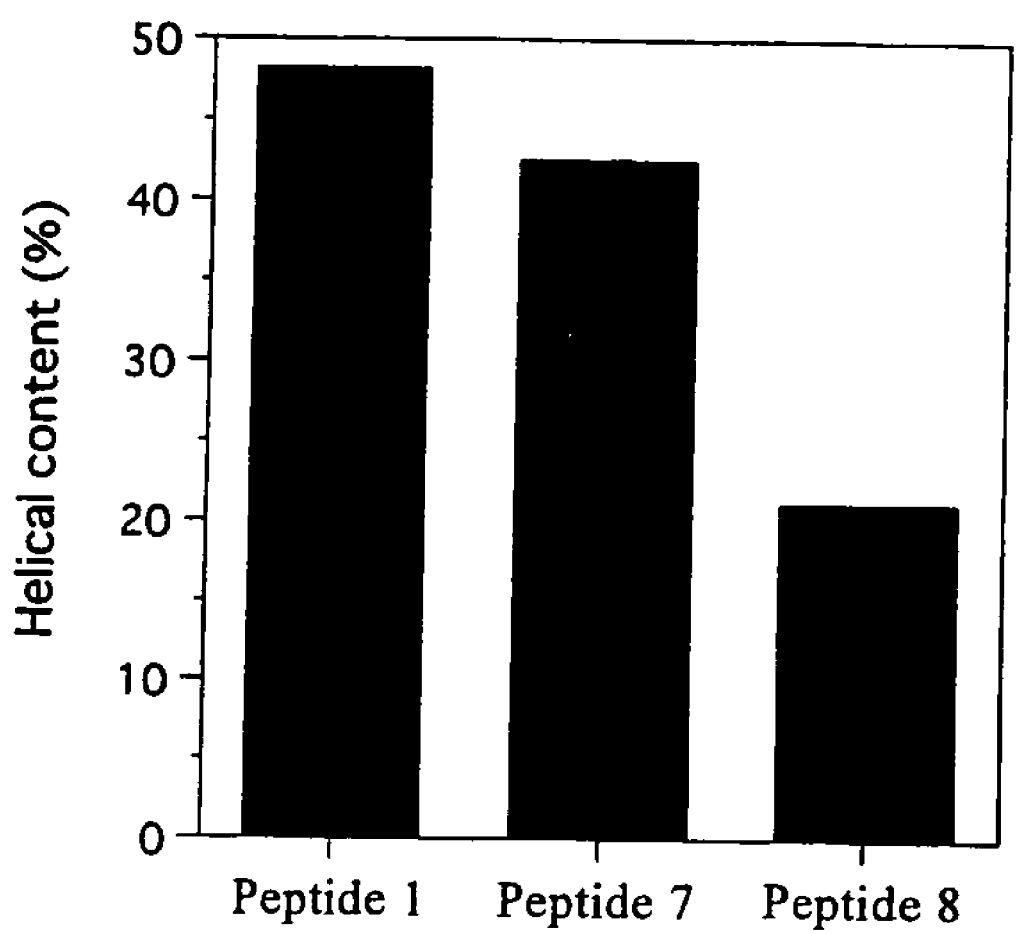
FIG. 2 shows the helical content in the higher-order structures of peptides 1, 7, and 8 calculated based on the method for higher-order structure analysis.

VIP (peptide 1, SEQ ID NO: 2), peptide 7 (SEQ ID NO: 8) corresponding to 25 residues at the N-terminus of VIP, and peptide 8 (SEQ ID NO: 9), which is a peptide 7 derivative with its methionine-17 being oxidized, were dissolved in a 20 mM Tris-HCl buffer (pH 7.4), and the circular dichroism spectra thereof were examined using the Jasco J-720 (Jasco Corporation). According to analytical calculation of higher-order structure by Greenfield et al., the helical content of peptide 1 was about 50% (FIG. 2). Although it was suggested that peptide 7 would retain a good deal of such higher-order structure, the helical content of peptide 8 with oxidized methionine was reduced to about half that of peptide 1, which indicates a remarkable structural change.

EXAMPLE 5

Pharmacological Activity of Peptide 7 and Peptide 8

Figure 3:
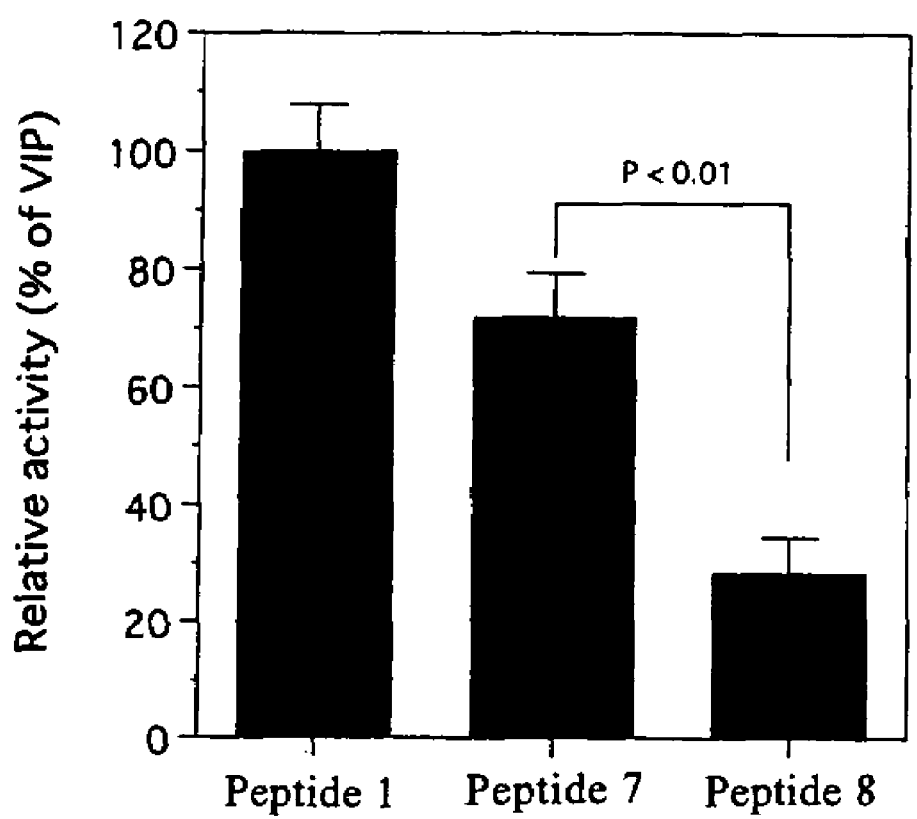
FIG. 3 shows the relative ratios of peptides 7 and 8 for inhibiting constriction of murine gastric smooth muscles in relation to peptide 1 (wild-type VIP).

9-week-old male ICR mice were preliminarily raised for 1 week and then used during the period in which they were aged 10 to 18 weeks. After the mice were subjected to cervical spine dislocation, abdominal operation was performed immediately thereafter for total gastric resection, and the interiors of the stomachs were thoroughly washed with physiologic saline to prepare specimens. The finished specimens were suspended in a Magnus tank (volume: 20 ml; temperature: 37° C.; load: 2.0 g; aeration with 95% $CO_2$ and 5% $CO_2$; Riken Kaihatsu). As a physiological solution, a Krebs-Henseleit Buffer Modified solution (Sigma) was used. The reaction was recorded on the recorder R-64M (Rika Denki) via an amplifier RMP-6004 (Nihon Kohden Corporation). In the experiment, specimens were installed on the Magnus apparatus, and 100 µl of carbachol solution (concentration: $6 \times 10^{-3}$ M) was added thereto after the baseline had been stabilized. A sample solution of purified peptide was added 10 minutes thereafter, and the relaxant effects on the specimens were observed. The effect of peptide 1 (wild-type VIP) against carbachol-induced constriction was determined to be 100%, and the maximal inhibition of smooth muscle constriction when peptide 7 or peptide 8 was added was determined. FIG. 3 relatively shows the maximal inhibition of murine gastric smooth muscle constriction at the final concentration of $10^{-6}$ M of peptides 1, 7, and 8. Activity of peptide 8 was significantly attenuated compared to that of peptide 7, which indicates the strong influence of oxidation of methionine residue. Such attenuated activity was found to be deeply correlated with the helical content of the compounds, based on Example 4. More specifically, oxidation of methionine residue in VIP/PACAP induces changes in higher-order structures at a molecular level and significantly influences activity.

EXAMPLE 6

Stability of Peptide 12

An adequate amount of peptide 12 was fractionated via weighing, dissolved in distilled water (1 mg/ml, Otsuka Distilled Water), and adjusted to pH levels of 6.0 and 7.0 with the aid of 0.1N NaOH. Further, peptide 12 was diluted to 10 µg/ml and then allowed to stand in an incubator at 40°

C. for 24 hours. Thereafter, reverse phase HPLC analysis was carried out (wavelength: 220 nm; mobile phase: acetonitrile (29%)/trifluoroacetic acid (0.1%); column: ODS-120T (Tosoh); column temperature: 25° C.) to examine the amount of remaining peptide 12. As a result, no significant generation of an unidentified peak was observed in either specimen at a pH level of 6.0 or 7.0. This suggests that peptide 12 was stable.

EXAMPLE 7

Stability of Peptides 4, 12, 21, and 23

Adequate amounts of peptides 4, 12, 21, and 23 were fractionated via weighing and then dissolved in distilled water (Otsuka Distilled Water) adjusted at pH levels of 6.0 and 7.0 to bring the final concentration to 10 µg/ml. The resulting solutions were allowed to stand in an incubator at 55° C. (FC-610, Advantec) for 3 days, and reverse phase HPLC analysis was carried out (wavelength: 220 nm; mobile phase: acetonitrile (29.5%)/trifluoroacetic acid (0.1%); column: ODS-120T (Tosoh); column temperature: 25° C.) to examine the quantities of remaining peptides 4, 12, 21, and 23. As shown in Table 5, stability of peptides 12, 21, and 23 was significantly improved compared to that of peptide 4. This was particularly apparent at pH 7.0.

TABLE 5

| Specimen | PH 6.0 | PH 7.0 |
| --- | --- | --- |
| Peptide 4 | 81% | 67% |
| Peptide 12 | 94% | 100% |
| Peptide 21 | 93% | 100% |
| Peptide 23 | 100% | 100% |

EXAMPLE 8

Stability of Peptides 4, 12, 21, and 23

Adequate amounts of peptides 4, 12, 21, and 23 were fractionated via weighing and then dissolved in distilled water (Otsuka Distilled Water) adjusted at the pH level of 7.0 to bring the final concentration to 100 µg/ml. The resulting solutions were allowed to stand in an incubator at 55° C. (FC-610, Advantec) for 0, 10, 20, and 30 days, respectively, and reverse phase HPLC analysis was carried out (wavelength: 220 nm; mobile phase: acetonitrile (29.5%)/trifluoroacetic acid (0.1%); column: ODS-120T (Tosoh); column temperature: 25° C.) to examine the amount of remaining peptides 4, 12, 21, and 23. As shown in Table 6, peptide 4 completely disappeared after storage for 10 days; however, peptides 12, 21, and 23 still remained 30 days later. This indicates that stability thereof was significantly improved.

TABLE 6

| Specimen | 0 day | 10 days | 20 days | 30 days |
| --- | --- | --- | --- | --- |
| Peptide 4 | 100% | 0% | 0% | 0% |
| Peptide 12 | 100% | 49% | 34% | 18% |
| Peptide 21 | 100% | 29% | 45% | 10% |
| Peptide 23 | 100% | 62% | 42% | 30% |

EXAMPLE 9

Stability of Peptides 4, 12, 21, and 23

Adequate amounts of peptides 4, 12, 21, and 23 were fractionated via weighing and then dissolved in phosphate buffers (aqueous solution of 0.001% sodium dihydrogen phosphate) adjusted to pH levels of 6.0 and 7.0 to bring the final concentration to 100 µg/ml. The resulting solutions were allowed to stand in a thermo-hygrostat (LH-20-11, Nagano Kagaku) at 40° C. and 75% RH for a week, and reverse phase HPLC analysis was carried out (wavelength: 220 nm; mobile phase: acetonitrile (29.5%)/trifluoroacetic acid (0.1%); column: ODS-120T (Tosoh); column temperature: 25° C.) to examine the quantities of remaining peptides 4, 12, 21, and 23. As shown in Table 7, stability of peptides 12, 21, and 23 was significantly improved compared to that of peptide 4.

TABLE 7

| Specimen | PH 6.0 | PH 7.0 |
| --- | --- | --- |
| Peptide 4 | 53% | 35% |
| Peptide 12 | 100% | 90% |
| Peptide 21 | 100% | 87% |
| Peptide 23 | 100% | 100% |

EXAMPLE 10

Stability of Peptides 4, 12, 21, and 23

Adequate amounts of peptides 4, 12, 21, and 23 were fractionated via weighing and then dissolved in phosphate buffer (an aqueous solution of 0.001% sodium dihydrogen phosphate) adjusted at the pH level of 7.0 to bring the final concentration to 100 µg/ml. The resulting solutions were allowed to stand in a thermo-hygrostat (LH-20-11, Nagano Kagaku) at 40° C. and 75% RH for 0, 10, 20, and 30 days, and reverse phase HPLC analysis was carried out (wavelength: 220 nm; mobile phase: acetonitrile (29.5%)/trifluoroacetic acid (0.1%); column: ODS-120T (Tosoh); column temperature: 25° C.) to examine the quantities of remaining peptides 4, 12, 21, and 23. As shown in Table 8, stability of peptides 12, 21, and 23 was significantly improved compared to that of peptide 4. Also, peptide 4 disappeared 30 days later; however, peptides 12, 21, and 23 still remained.

TABLE 8

| Specimen | 0 day | 10 days | 20 days | 30 days |
| --- | --- | --- | --- | --- |
| Peptide 4 | 100% | 28% | 13% | 0% |
| Peptide 12 | 100% | 84% | 86% | 73% |
| Peptide 21 | 100% | 100% | 76% | 59% |
| Peptide 23 | 100% | 98% | 89% | 73% |

EXAMPLE 11

Inhibitory Effect on Gastric Peristaltic Movement

Inhibitory effects of peptides 9, 10, and 33 on gastric peristaltic movements were examined in the same manner as in Example 5. 9-week-old male ICR mice were employed. After the mice were subjected to cervical spine dislocation, abdominal operation was performed immediately thereafter for total gastric resection, and the interiors of the stomachs were thoroughly washed with physiologic saline to prepare specimens. The finished specimens were suspended in a Magnus tank (volume: 20 ml; temperature: 37° C.; load: 2.0 g; aeration with 95% $O_2$ and 5% $CO_2$; Riken Kaihatsu). As a physiological solution, a Krebs-Henseleit Buffer Modified solution (Sigma) was used. The reaction was recorded on the recorder R-64M (Rika Denki) via an amplifier RMP-6004 (Nihon Kohden Corporation). In the experiment, specimens were installed on the Magnus apparatus, and a carbachol solution ($3\times10^{-6}$ M) was added thereto after the baseline had been stabilized. When constriction was stabilized, test peptides ($10^{-6}$ M) were added, and the relaxant effects on the specimens were observed. The degree of constriction before the addition of carbachol was determined to be 0%, that after stabilization following the addition thereof was determined to be 100%, and the level of gastric constriction inhibition was determined when the sample solutions were added. Table 9 shows the level of each substance for inhibiting constriction 15 minutes after drug administration. Table 9 exhibits the level of each substance (peptides 10 and 33) for inhibiting constriction providing that the level of peptide 9, which was the control drug, was 100.

TABLE 9

| Substance | Level of constriction inhibition |
|---|---|
| Peptide 9 | 100 |
| Peptide 10 | 227 |
| Peptide 33 | 160 |

EXAMPLE 12

Relaxant Effect on Bronchial Smooth Muscle

Whether or not peptides 12, 21, and 23 were capable of temporarily constricting the dilated bronchial smooth muscle was examined in the manner described below.

Figure 4:
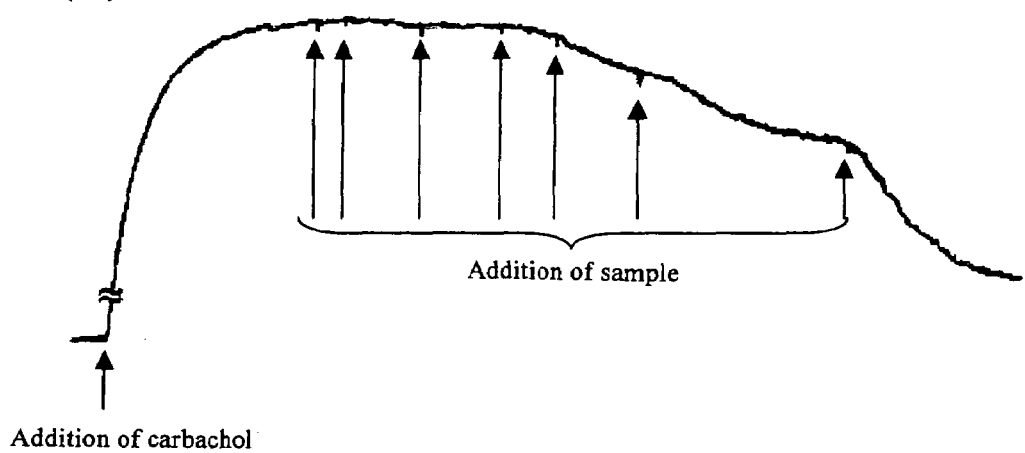
FIG. 4(A) shows the relaxant effect of peptide 12 on the bronchi.
FIG. 4(B) shows that of peptide 21.
FIG. 4(C) shows that of peptide 23.
Figure 4:
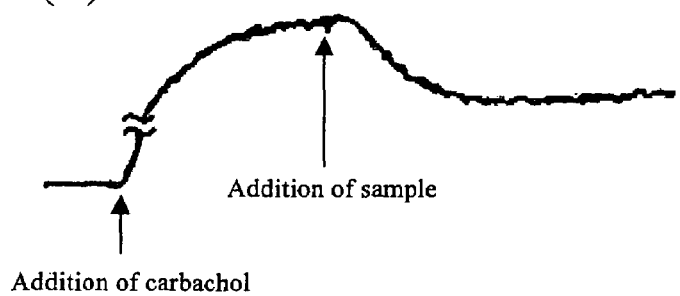
Figure 4:
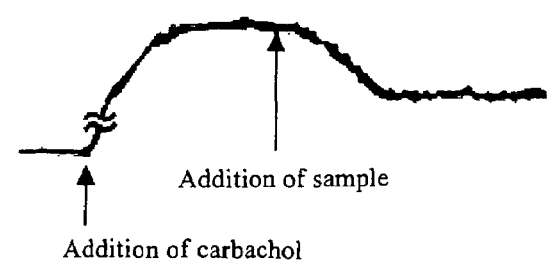

7-week-old Hartley male guinea pigs (440 g, Japan SLC) were sacrificed via bleeding from the femoral artery under anesthesia, and the thoraxes thereof were opened to extirpate the tracheas. Fatty tissues and the like adhering to the tracheas were removed as fully as possible, the removed tissues were sliced along cartilages to a width covering 4 or 5 cartilages, and cartilages located opposite to the esophagus were sliced lengthwise to prepare sections. Sections obtained from the upper, middle, and lower esophagi were employed as specimens. The specimens were suspended in a Magnus tank (volume: 20 ml; temperature: 37° C.; load: 0.5 g; aeration with 95% $O_2$ and 5% $CO_2$). As a physiological solution, a Krebs-Henseleit Buffer Modified solution (Sigma) was used. The reaction was recorded on the recorder R-64 M (Rika Denki) via an amplifier RMP-6004 (Nihon Kohden Corporation) using an isometric transducer (TB-611T, Nihon Kohden Corporation). After carbachol ($3\times10^{-7}$ M)-induced constriction was stabilized, cumulative administration of peptide 12 ($10^{-9}$ M to $3\times10^{-6}$ M) was made, and single administrations of peptide 21 and of peptide 23 ($3\times10^{-6}$ M) were made. After the measurement, isoproterenol ($10^{-6}$ M) was administered, the value attained at this time was determined to be "100% relaxation," and the degree of relaxation for each test substance was determined based thereon. This demonstrates that peptides 12, 21, and 23 had an apparent peptide-addition-dependent effect of relaxing the trachea as shown in FIG. 4.

EXAMPLE 13

Effect of Inducing Neurite Formation

Figure 5:
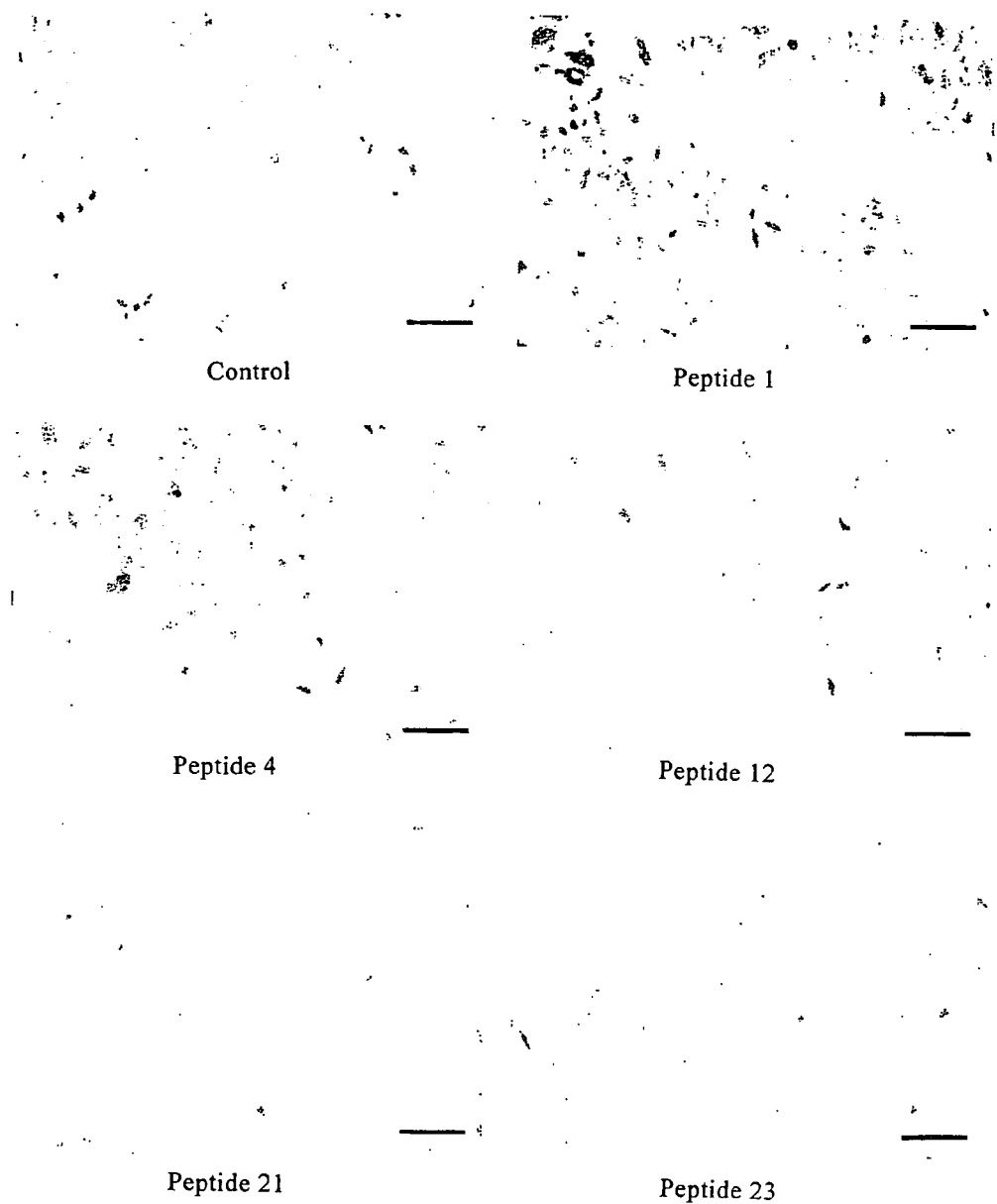
FIG. 5 shows the effects of inducing neurite formation of the control (a specimen where there is no peptide addition), peptide 1 (wild-type VIP), peptide 4, peptide 12, peptide 21, and peptide 23.

Effect of peptides 1, 4, 12, 21, and 23 for inducing neurite formation were tested in the manner described below. PC-12 cells were cultured in Dulbecco's modified minimum essential medium (DMEM) containing 5% horse serum and 5% fetal calf serum in the presence of 5% $CO_2$ and 95% air at 37° C. Cells were separated from the culture flask with the aid of trypsin, counted using a cytometer, and then the concentration was adjusted to $1.0\times10^4$ cells/ml. The cell-containing liquid medium was added to a Biocoat type IV collagen-coated 24-well dish in amounts of 1 ml each and then cultured in the presence of 5% $CO_2$ and 95% air at 37° C. for 24 hours. The medium was replaced 24 hours later, and peptides (100 nM) were added at that time. The resultant was continuously cultured for 3 days and then photographed. FIG. 5 shows the photographs. The scale bar in each photograph represents 100 μm. As shown in the photographs, peptides 4, 12, 21, and 23 significantly induced neurite formation compared to the case of the control (a specimen without peptide) and peptide 1 (wild-type VIP).

EXAMPLE 14

Neuroprotective Effect

Figure 6:
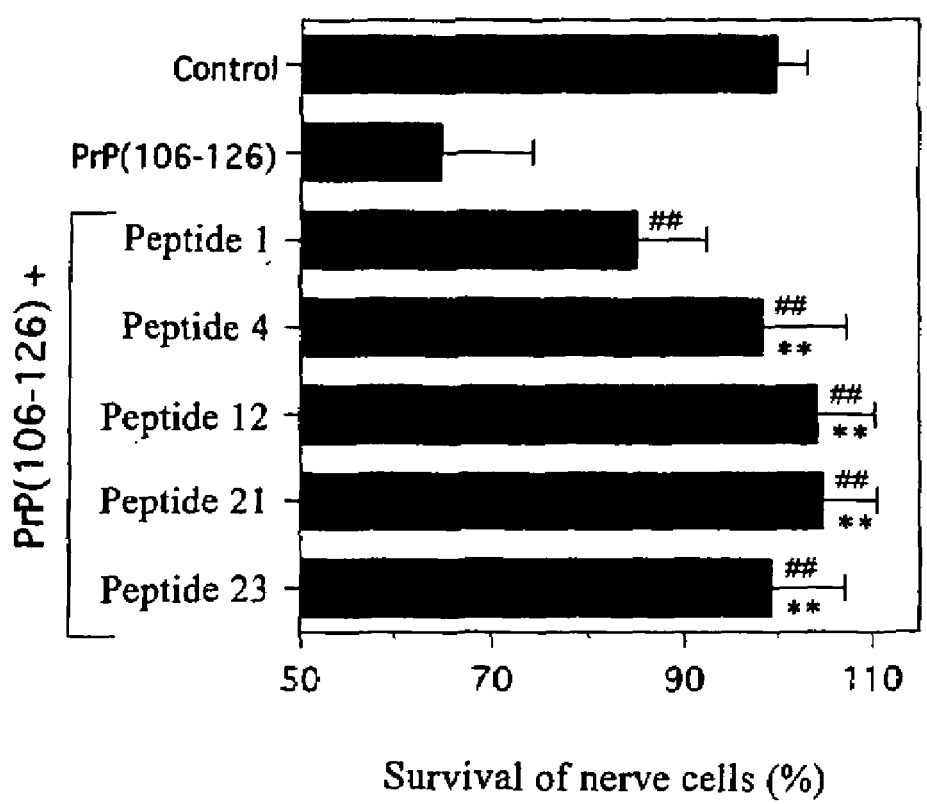
FIG. 6 shows the effects of peptides 4, 12, 21, and 23 for protecting nerves against abnormal prions (PrP 106-126), wherein "##" represents a significant difference from a specimen in the absence of peptide (P<0.01) and "**" represents a significant difference from peptide 1 (P<0.01).

It has been already verified that a normal prion is transformed to an abnormal prion via conformational conversion (J. Neurochem, 2000, vol. 75, pp. 2536-2545). Thus, cell death caused by abnormal folding of the prion protein (106-126) was examined using rat-pheochromocytoma-derived PC12 cells, which are used as a model for research into the brain and the nervous system. The PC12 cells were cultured in Dulbecco's modified minimum essential medium (DMEM) containing 5% horse serum and 5% fetal calf serum in the presence of 5% $CO_2$ and 95% air at 37° C. The PC12 cells were separated from the culture flask with the aid of trypsin and then cultured on a 96-well culture plate ($10^4$ cells/well). Prions (106-126, 50 μM, American Peptide Company Inc.) and $10^{-7}$ M neuropeptides (peptides 1, 4, 12, 21, and 23) were added to the cultured PC12 cells, viable cell counts were calculated by WST-8 assay, and the degree of the neuroprotective effect against abnormal prions (PrP 106-126) was quantified. The results are shown in FIG. 6. The viable cell counts of peptide 1 (wild-type VIP) were significantly larger than those of specimens containing no peptide (##, P<0.01), and peptide 1 exhibited a significant neuroprotective effects. Furthermore, the neuroprotective effects of peptides 4, 12, 21, and 23 were significantly higher than that of peptide 1 (**, P<0.01).

EXAMPLE 15

Production of Formulation for Manufacturing Inhalation Formulation and Nasal Drops Formulation for manufacturing inhalation formulation and nasal drops was produced basically in accordance with the method for producing powder formulations disclosed in JP Patent Publication (Kokai) No. 2003-34652.

Conditions for Grinding

| Equipment used: | A-O-Jet Mill (Seishin Enterprise Co., Ltd.) |
| --- | --- |
| Means for feeding materials: | Automatic feeder |
| Feeding air pressure: | 6.0 kg/cm² G |
| Grinding air pressure: | 6.5 kg/cm² G |
| Dust collection: | Collecting bag |

In the method described above, peptides 4, 12, 21, and 23 were diluted with lactose or erythritol. Erythritol carriers (average particle diameter of 70 μm) or lactose carriers (average particle diameter of 50 μm) were mixed therewith using an unelectrified bag in a ratio of finely ground product: carrier of 0.4:1.

EXAMPLE 16

Production of Eye Drops

| Neuropeptide | 10 mg |
| --- | --- |
| Boric acid | 700 mg |
| Sodium borate | adequate amount |
| Sodium chloride | 500 mg |
| Hydroxymethylcellulose | 0.5 g |
| Edetate sodium | 0.005 mg |
|  | pH 7.0 |
| Sterilized purified water | balance (100 ml in total) |

Sterilized purified water (80 ml) was heated to about 80° C., hydroxymethylcellulose was added thereto, the resulting mixture was agitated, and the temperature of the liquid was cooled to room temperature. Neuropeptide, sodium chloride, boric acid, edetate sodium, and benzalkonium chloride were added and dissolved in the above liquid. An adequate amount of sodium borate was added to bring the pH level to 7.0. The total amount of the solution was accurately adjusted to 100 ml with the addition of sterilized purified water.

Peptides 4, 12, 21, and 23 were employed as neuropeptides.

EXAMPLE 17

Production of Injection Preparation

| Neuropeptide | 10 mg |
| --- | --- |
| Sodium chloride | 900 mg |
| 1 N Sodium hydroxide | adequate amount |
| Distilled water for injection | balance (100 ml in total) |

These ingredients were aseptically mixed in accordance with a conventional technique to prepare injection preparations. Peptides 4, 12, 21, and 23 were employed as neuropeptides.

All publications, patents, and patent applications cited herein are incorporated herein by reference in their entirety.

INDUSTRIAL APPLICABILITY

The present invention can provide a PACAP/VIP derivative that can be stored for a long period of time and can avoid unexpected side effects resulting from the generation of by-products.

Sequence Listing Free Text
SEQ ID NO: 1: synthetic peptide
SEQ ID NO: 2: synthetic peptide
SEQ ID NO: 3: synthetic peptide
SEQ ID NO: 4: synthetic peptide
SEQ ID NO: 5: synthetic peptide
SEQ ID NO: 6: synthetic peptide
SEQ ID NO: 7: synthetic peptide
SEQ ID NO: 8: synthetic peptide
SEQ ID NO: 9: synthetic peptide
SEQ ID NO: 10: synthetic peptide
SEQ ID NO: 11: synthetic peptide
SEQ ID NO: 12: synthetic peptide
SEQ ID NO: 13: synthetic peptide
SEQ ID NO: 14: synthetic peptide
SEQ ID NO: 15: synthetic peptide
SEQ ID NO: 16: synthetic peptide
SEQ ID NO: 17: synthetic peptide
SEQ ID NO: 18: synthetic peptide
SEQ ID NO: 19: synthetic peptide
SEQ ID NO: 20: synthetic peptide
SEQ ID NO: 21: synthetic peptide
SEQ ID NO: 22: synthetic peptide
SEQ ID NO: 23: synthetic peptide
SEQ ID NO: 24: synthetic peptide
SEQ ID NO: 25: synthetic peptide
SEQ ID NO: 26: synthetic peptide
SEQ ID NO: 27: synthetic peptide
SEQ ID NO: 28: synthetic peptide
SEQ ID NO: 29: synthetic peptide
SEQ ID NO: 30: synthetic peptide
SEQ ID NO: 31: synthetic peptide
SEQ ID NO: 32: synthetic peptide
SEQ ID NO: 33: synthetic peptide
SEQ ID NO: 34: synthetic peptide

The invention claimed is:

1. A peptide comprising at least 23 amino acid residues from the N-terminal of the peptide, or a pharmaceutically acceptable salt thereof, according to formula (I):

(SEQ ID NO:1)
His-Ser-Asp-Ala-variable A-Phe-Thr-variable B- variable C-Tyr-variable D-Arg-variable E-Argvariable F-Gln-variable G-Ala-Val-variable H- variable I-Tyr-Leu-Ala-Ala-variable J-variable K- variable L (I)

wherein variable A represents Val or Ile; variable B represents Asp, Glu, or Ala; variable C represents Asn or Ser; variable D represents Thr or Ser; variable E represents Leu or Tyr; variables F, H, and I each independently represent Lys or Arg; variable G represents Leu or Nle; variable J represents Ile or Val; variable K represents Leu, Leu-Asn, Leu-Gly, Leu-Gly-Lys, Leu-Gly-Arg, Leu-Gly-Lys-Lys, Leu-Gly-Lys-Arg, Leu-Gly-Arg-Arg, Leu-Gly-Lys-Arg-Tyr-Lys-Gln-Arg-Val-Lys-Asn-Lys, or Leu-Gly-Arg-Arg-Tyr-Arg-Gln-Arg-Val-Arg-Asn-Arg; and variable L represents a moiety attached to the α-carboxyl group of the C-terminal amino acid, wherein said moiety is an —NH$_2$ or —OH.

2. The peptide, or a pharmaceutically acceptable salt thereof, according to claim 1, which consists of 23 amino acid residues from the N-terminus of the peptide according to formula (I), wherein variable A represents Val; variable B represents Asp; variable C represents Asn; variable D represents Thr; variable E represents Leu; variables F, H, and I each independently represent Arg; variable G represents Leu; and variable L represents an —NH$_2$ moiety attached to the α-carboxyl group of the C-terminal amino acid.

3. The peptide, or a pharmaceutically acceptable salt thereof, according to claim 1, wherein variables F, H, and I each independently represent Arg; variable G represents Leu; variable K represents Leu-Gly-Arg-Arg; and variable L represents an —NH$_2$ moiety attached to the α-carboxyl group of the C-terminal amino acid.

4. The peptide, or a pharmaceutically acceptable salt thereof, according to claim 3, wherein variable A represents Val; variable B represents Asp; variable C represents Asn; variable D represents Thr; variable E represents Leu; and variable J represents Ile.

5. The peptide, or a pharmaceutically acceptable salt thereof, according to claim 3, wherein variable A represents Val; variable B represents Glu; variable C represents Asn; variable D represents Thr; variable E represents Leu; and variable J represents Ile.

6. The peptide, or a pharmaceutically acceptable salt thereof, according to claim 3, wherein variable A represents Val; variable B represents Ala; variable C represents Asn; variable D represents Thr; variable E represents Leu; and variable J represents Ile.

7. The peptide, or a pharmaceutically acceptable salt thereof, according to claim 3, wherein variable A represents Val; variable B represents Asp; variable C represents Asn; variable D represents Thr; variable E represents Leu; and variable J represents Val.

8. The peptide, or a pharmaceutically acceptable salt thereof, according to claim 3, wherein variable A represents Ile; variable B represents Asp; variable C represents Ser; variable D represents Ser; variable E represents Tyr; and variable J represents Val.

9. The peptide, or a pharmaceutically acceptable salt thereof, according to claim 1, wherein variable A represents Ile; variable B represents Asp; variable C represents Ser; variable D represents Ser; variable E represents Tyr; variables F, H, and I each independently represent Arg; variable G represents Leu; variable J represents Val; variable K represents Leu-Gly-Arg-Arg-Tyr-Arg-Gln-Arg-Val-Arg-Asn-Arg; and variable L represents an —NH$_2$ moiety attached to the α-carboxyl group of the C-terminal amino acid.

10. The peptide, or a pharmaceutically acceptable salt thereof, according to claim 1, which consists of 23 amino acid residues from the N-terminus of the peptide according to formula (I), wherein variable A represents Ile; variable B represents Asp; variable C represents Ser; variable D represents Ser; variable E represents Tyr; variables F, H, and I each independently represent Arg; variable G represents Leu; and variable L represents an —NH$_2$ moiety attached to the α-carboxyl group of the C-terminal amino acid.

11. A pharmaceutical composition comprising one or more biologically active peptides according to claim 1, or a pharmaceutically acceptable salt thereof.

12. A pharmaceutical composition comprising one or more biologically active peptides according to claim 1, or a pharmaceutically acceptable salt thereof, which is present as an active ingredient within the pharmaceutical composition in an amount of at least 50% by weight based on the total weight percent of the biologically active peptides contained within the pharmaceutical composition.

13. A method of relaxing the bronchial smooth muscle, wherein said method comprises administering to a patient in need thereof a therapeutically effective amount of the peptide according to claim 1, or a pharmaceutically acceptable salt thereof.

14. A method of relaxing the bronchial smooth muscle, wherein said method comprises administering to a patient in need thereof a therapeutically effective amount of the pharmaceutical composition according to claim 11.

15. A method of relaxing the bronchial smooth muscle, wherein said method comprises administering to a patient in need thereof a therapeutically effective amount of the pharmaceutical composition according to claim 12.

16. A method of inhibiting the movement in the gastrointestinal tract, wherein said method comprises administering to a patient in need thereof a therapeutically effective amount of the peptide according to claim 1, or a pharmaceutically acceptable salt thereof.

17. A method of inhibiting the movement in the gastrointestinal tract, wherein said method comprises administering to a patient in need thereof a therapeutically effective amount of the pharmaceutical composition according to claim 11.

18. A method of inhibiting the movement in the gastrointestinal tract, wherein said method comprises administering to a patient in need thereof a therapeutically effective amount of the pharmaceutical composition according to claim 12.

* * * * *